United States Patent
Tierney et al.

(10) Patent No.: US 10,561,669 B2
(45) Date of Patent: *Feb. 18, 2020

(54) ORAL QUETIAPINE SUSPENSION FORMULATIONS WITH EXTENDED SHELF LIFE AND ENHANCED BIOAVAILABILITY

(71) Applicant: TLC THERAPEUTICS, LLC, Pikesville, MD (US)

(72) Inventors: Carl Tierney, Leeds (GB); Andrew Gardner, Leeds (GB); Jan Pick-Katolik, Leeds (GB); Stacey Powell, Leeds (GB); Mark Foley, Leeds (GB); Laurence Ramsey, Leeds (GB); Andrew Hardeman, Leeds (GB)

(73) Assignee: TLC THERAPEUTICS, LLC, Pikesville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/904,086

(22) Filed: Feb. 23, 2018

(65) Prior Publication Data

US 2018/0360844 A1 Dec. 20, 2018

Related U.S. Application Data

(63) Continuation of application No. 15/627,087, filed on Jun. 19, 2017, now Pat. No. 9,993,486.

(51) Int. Cl.
*A61K 31/554* (2006.01)
*A61J 1/14* (2006.01)
(Continued)

(52) U.S. Cl.
CPC ............ *A61K 31/554* (2013.01); *A61J 1/1412* (2013.01); *A61J 1/1468* (2015.05); *A61K 45/06* (2013.01); *B65B 3/003* (2013.01); *B65B 7/28* (2013.01)

(58) Field of Classification Search
CPC ...... A61K 9/16; A61K 9/1682; A61K 9/1629; A61K 31/554; A61K 45/06; A61K 9/107;
(Continued)

(56) References Cited

U.S. PATENT DOCUMENTS 6,599,897 B1 7/2003 Brown
6,716,416 B2 4/2004 Rabinowitz
(Continued)

FOREIGN PATENT DOCUMENTS

WO 2007062339 A2 5/2007

OTHER PUBLICATIONS

Technical publication, Exteeending shelf life for you and the patient, East Stone (UK) (2014).
(Continued)

*Primary Examiner* — Carlos A Azpuru
(74) *Attorney, Agent, or Firm* — Nevrivy Patent Law Group P.L.L.C.

(57) ABSTRACT

A quetiapine fumarate composition for oral administration is provided comprising a pharmaceutically acceptable salt or solvate of quetiapine existing as a suspension in an aqueous carrier agent. The inventive liquid formulation demonstrates high bioavailability consistent with approved dosage forms, low agglomeration, reduced content of excipients commonly used in solid oral dosage forms and extended shelf life stability. Also provided is a method of manufacturing a liquid quetiapine suspension composition for oral administration and methods of administering therapeutically effective dosages of an oral liquid quetiapine suspension composition to patients in need thereof.

15 Claims, 23 Drawing Sheets

(51) Int. Cl.
  *A61K 45/06* (2006.01)
  *B65B 3/00* (2006.01)
  *B65B 7/28* (2006.01)
(58) Field of Classification Search
  CPC ........ A61K 9/0095; A61K 47/24; B65B 7/28;
  A61J 1/1412; A61J 1/1468
  See application file for complete search history.

(56) References Cited

U.S. PATENT DOCUMENTS

| | | | |
|---|---|---|---|
| 7,022,692 B2 | 4/2006 | Brown |
| 7,071,331 B2 | 7/2006 | Diller |
| 7,078,020 B2 | 7/2006 | Rabinowitz |
| 7,238,686 B2 | 7/2007 | Parthasaradhi |
| 7,304,047 B2 | 12/2007 | Brown |
| 7,338,948 B2 | 3/2008 | Robertson |
| 7,488,821 B2 | 2/2009 | Rao |
| 7,585,493 B2 | 9/2009 | Hale |
| 7,601,337 B2 | 10/2009 | Rabinowitz |
| 7,611,728 B2 | 11/2009 | Kidane |
| 7,794,750 B2 | 9/2010 | Naringrekar |
| 7,863,277 B1 | 1/2011 | Herman |
| 7,959,948 B2 | 6/2011 | Jansen |
| 8,003,637 B2 | 8/2011 | Liu |
| 8,034,805 B2 | 10/2011 | Hradil |
| 8,044,038 B2 | 10/2011 | Rummakko |
| 8,044,039 B2 | 10/2011 | Grumann |
| 8,057,811 B2 | 11/2011 | Surman |
| 8,088,814 B2 | 1/2012 | Muller |
| 8,101,597 B2 | 1/2012 | Dixit |
| 8,173,637 B2 | 5/2012 | Liu |
| 8,216,609 B2 | 7/2012 | Vaya |
| 8,389,510 B2 | 3/2013 | Black |
| 8,389,716 B2 | 3/2013 | Serafini |
| 8,420,807 B2 | 4/2013 | Grumann |
| 8,440,223 B2 | 5/2013 | Velhal |
| 8,512,759 B1 | 8/2013 | McMahen |
| 8,591,947 B2 | 11/2013 | Vergez |
| 8,598,119 B2 | 12/2013 | Mates |
| 8,623,861 B2 | 1/2014 | Li |
| 8,632,805 B2 | 1/2014 | Gandha |
| 9,757,371 B2 | 9/2017 | Haswani |
| 9,993,486 B1 * | 6/2018 | Tierney ................ A61K 9/1629 |
| 2003/0216376 A1 | 11/2003 | Lifshitz-Liron |
| 2004/0058909 A1 | 3/2004 | Goldstein |
| 2004/0242562 A1 | 12/2004 | Reddy |
| 2005/0026900 A1 | 2/2005 | Goldstein |
| 2005/0158383 A1 | 7/2005 | Boehm |
| 2006/0063927 A1 | 3/2006 | Etlin |
| 2006/0223994 A1 | 10/2006 | Rao |
| 2007/0031340 A1 | 2/2007 | Hale |
| 2008/0108596 A1 | 5/2008 | Lee |
| 2009/0069292 A1 | 3/2009 | Korey |
| 2013/0273158 A1 | 10/2013 | Reddy |
| 2014/0030329 A1 | 1/2014 | Liu |
| 2014/0161748 A1 | 6/2014 | Li |
| 2016/0041192 A1 | 2/2016 | McIntire |

OTHER PUBLICATIONS

Quetiapine Fumarate 40-mg/mL Nonaqueous Oral Suspension, International Journal of Pharmaceutical Compounding, 15:342 (2011).
Drug Name: Quetiapine. Michigan Collaborative Standardization of Compounded Oral Liquids (2013).
Technical publication, Nova Laboratories Ltd. (2013).
Narala et al., Preparation, Characterization and Evaluation of Quetiapine Fumarate Solid Lipid Nanoparticles to Improve the Oral Bioavailability, Journal of Pharmaceutics, 2013:1-7 (2013).
Parvathi et al., Preparation and Evaluation of Quetiapine Fumarate Microemulsions: A Novel Delivery System, Asian Journal of Pharmaceutical and Clinical Research, 7:208-213 (2014).
Shantaram et al., Formulation and evaluation of hydrogel based nano crystals of Quetiapine, Carib.j.SciTech, 4:951-962 (2016).
Technical publication, 'Specials' Guidance: suggested alternatives for some commonly prescribed special order medicines, Herefordshire Clinical Commissioning Group (2013).
FDA Clinical Pharmacology/Biopharmaceutics Review for NDA: 20-639 (pp. 40-43) (1997).
Quetiapine Rosemont 20mg/ml Oral Suspension, Rosemont (May 2016).
U.S. Office Action from U.S. Appl. No. 15/627,087, dated Dec. 5, 2017.

* cited by examiner

Fig. 2

| Excipient | Quality Specification | Quetiapine Suspension mg/5ml | | | | Use |
|---|---|---|---|---|---|---|
| | | 12.5 | 25 | 100 | 200 | |
| | | Concentration (%w/v) | | | | |
| Citric Acid Monohydrate | USP | 0.907 | 0.907 | 1.814 | 1.814 | Buffer Salt |
| Di-Sodium Hydrogen Phosphate Dihydrate | USP | 2.024 | 2.024 | 4.048 | 4.048 | |
| Sucralose | NF | 0.20 | 0.20 | 0.20 | 0.20 | Intense Sweetener |
| Simethicone Emulsion (Q7-2587 30%) | USP | 0.033 | 0.066 | 0.066 | 0.10 | Anti-Foam Agent |
| Propylene Glycol | USP | 3.00 | 3.00 | 3.00 | 3.00 | Co-Solvent for Preservatives |
| Methyl Hydroxybenzoate | NF | 0.147 | 0.147 | 0.147 | 0.147 | Antimicrobial Preservative |
| Propyl Hydroxybenzoate | NF | 0.037 | 0.037 | 0.037 | 0.037 | |
| Xanthan Gum | NF | 0.40 | 0.40 | 0.40 | 0.40 | Suspending Agent |
| Lemon Flavor | HSE | 0.20 | 0.20 | 0.20 | 0.20 | Flavor/Taste Masking |
| Citric Acid Monohydrate (as a 10%w/v Solution) | HSE | qs | qs | qs | qs | pH adjustment |
| Disodium Hydrogen Phosphate Dihydrate (as a 10%w/v Solution) | HSE | qs | qs | qs | qs | |
| Purified Water | USP | to 100.0 | to 100.0 | to 100.0 | to 100.0 | Diluent |

FDA=Food and Drug Administration; NF=National Formulary; QS=quantity sufficient; USP=United States Pharmacopeia; HSE: In-house specification

Fig. 4

| In-process control tests | Purpose | Methods | In-process limits |
|---|---|---|---|
| Stirring time | Ensure complete dissolution and homogeneity of the suspension. | Time chronometer and visual inspection | Comply |
| pH | Ensure the correct preservation of the solution. | pH meter | 5.2 -5.8 |
| Final Volume | Ensure the compliance with unit formula | Weighing | Maximum 100L |

Fig. 6

Degradant % (RRT 0.22) / Quetiapine %

| API Source | A | B | C | D |
|---|---|---|---|---|
| Control | 0.05 / 99.54 | <0.03 / 99.55 | <0.03 / 99.58 | 0.07 / 98.96 |
| Heat | 0.06 / 99.46 | <0.03 / 98.95 | <0.03 / 99.26 | 0.07 / 98.62 |
| Metal | 0.05 / 97.62* | <0.03 / 100.00 | <0.03 / 95.08* | 0.07 / 99.23 |
| Base | 0.06 / 98.76 | <0.03 / 98.80 | <0.03 / 98.73 | 0.07 / 98.65 |

Acid

| API Source | Degradant | Lactam % | Quetiapine % |
|---|---|---|---|
| A | 0.62 | 0.51 | 97.49 |
| B | 0.50 | 0.37 | 97.05 |
| C | 0.51 | 0.39 | 97.50 |
| D | 0.55 | 0.37 | 97.72 |

Peroxide

| API Source | Degradant 1 | Degradant 2 | Degradant 3 | Piperazine % | Lactam % | Quetiapine % |
|---|---|---|---|---|---|---|
| A | 0.28 | 10.77 | 1.03 | 0.06 | 0.10 | 86.06 |
| B | 0.30 | 11.76 | 1.18 | 0.03 | 0.10 | 85.03 |
| C | 0.44 | 12.09 | 1.29 | 0.05 | 0.12 | 83.94 |
| D | 0.51 | 10.71 | 1.15 | 0.04 | 0.10 | 85.49 |

Fig. 7

| API Source | Product Specification | Starting Particle Diameter | Dissolution Recovery @ 45mins | Particle Size d(v,0.9) μm at Release (14 days) @ 5 °C |
|---|---|---|---|---|
| Manufacturer C Lot 2 | USP | D (v, 0.9) = 21 μm | 98.66 | 45.16 |
| Manufacturer B Lot 2 | USP | D (v, 0.9) = 31 μm | 91.43 | 94.822 |
| Manufacturer A Lot 1 | USP | D (v, 0.9) = 33 μm | 94.59 | 71.319 |
| Manufacturer D Lot 2 | USP | D (v, 0.9) = 37 μm | 81.90 | 148.359 |
| Manufacturer D Lot 1 | USP | D (v, 0.9) = 45 μm | 88.65 | 118.664 |
| Manufacturer C Lot 1 | USP | D (v, 0.9) = 51 μm | 94.38 | 61.76 |
| Manufacturer A Lot 2 | USP | D (v, 0.9) = 53 μm | 93.55 | 85.324 |
| Manufacturer B Lot 1 | USP | D (v, 0.9) = 58 μm | 76.42 | 156.778 |

Fig. 8

| Raw Material Lot No. | Strength | Raw Material Particle Size | | |
|---|---|---|---|---|
| | | d (0.1) | d (0.5) | d (0.9) |
| G33978 | 100mg/5ml | 12.598 | 59.447 | 217.850 |
| G33977 | 100mg/5ml | 10.361 | 31.311 | 63.321 |
| G40697 | 100mg/5ml | 8.074 | 22.687 | 47.632 |

Fig 9A

| Raw Material Lot No. | Strength | Relative Particle Size | Time (min) | | | | | |
|---|---|---|---|---|---|---|---|---|
| | | | 0 | 10 | 15 | 30 | 45 | 60 |
| G33978 | 100mg/5ml | High | 0.00 | 42.82 | 50.92 | 56.16 | 58.65 | 60.11 |
| G33977 | 100mg/5ml | Medium | 0.00 | 65.90 | 74.90 | 79.23 | 83.06 | 85.02 |
| G40697 | 100mg/5ml | Low | 0.00 | 61.26 | 74.62 | 83.86 | 87.23 | 89.06 |

Fig. 11

| Quetiapine Polymorph | Reference |
|---|---|
| Crystalline Form 1 | *See WO03080065 and US20040242562* |
| Crystalline Form 2 | *See US20030216376 and US20040242562* |
| Crystalline Form 3 | *See US20030216376* |
| Amorphous Form 4 | *See US20060223994* |
| Alternate Amorphous | *See US20040242562* |

Fig. 14

| Literature Values | API | 12.5ml/5ml | 25ml/5ml | 100mg/5ml | 200mg/5ml |
|---|---|---|---|---|---|
| 7.4 | 7.38 | 7.33 | 7.36 | 7.27 | 7.37 |
| 9.2 | 9.17 | 9.16 | 9.17 | 9.22 | 9.17 |
| 11.6 | 11.63 | 11.55 | 11.62 | 11.67 | 11.62 |
| 13.3 | 13.34 | 13.27 | 13.34 | 13.41 | 13.34 |
| 15.3 | 15.26 | 15.25 | 15.17 | 15.33 | 15.25 |
| 16.2 | 16.23 | 16.23 | 16.24 | 16.28 | 16.22 |
| 16.7 | 16.64 | 16.64 | 16.65 | 16.72 | 16.67 |
| 17.7 | 17.66 | 17.62 | 17.63 | 17.71 | 17.63 |
| 19.7 | 19.69 | 19.66 | 19.68 | 19.74 | 19.67 |
| 20.0 | 19.98 | 20.01 | 20.02 | 20.02 | 19.96 |
| 21.1 | 21.08 | 21.08 | 21.13 | 21.11 | 21.06 |
| 21.8 | 21.79 | 21.74 | 21.80 | 21.84 | 21.77 |
| 22.3 | 22.27 | 22.25 | 22.27 | 22.25 | 22.27 |
| 23.3 | 23.33 | 23.27 | 23.37 | 23.33 | 23.28 |
| 25.1 | 25.04 | 25.04 | 25.06 | 25.10 | 25.03 |

Fig. 15

| Excipient | | Maximum Daily Intake (mg/Kg/day) | Amount per 5ml of product (mg) | Amount supplied by maximum daily intake of product (mg) | | |
|---|---|---|---|---|---|---|
| | | | | 12.5mg/5ml (64x5ml) | 25mg/5ml (32x5ml) | 100mg/5ml (8x5ml) |
| Sucralose | | 15.00 | 10.00 | 640.00 | 320.00 | 80.00 |
| Simethicone Emulsion 30% | 12.5 | 1.50 | 0.50 | 32.00 | | |
| | 25 | | 0.99 | | 31.68 | |
| | 100 | | 0.99 | | | 7.92 |
| Total Propylene Glycol (PG) (including PG in Lemon Flavor) | | 25.00 | 159.56 | 10211.84 | 5105.92 | 1276.48 |
| TotalMethyl & Propyl Hydroxybenzoate | | 10.00 | 9.20 | 588.80 | 294.40 | 73.60 |

Fig. 16A

| Quetiapine 12.5mg/5ml ||||
|---|---|---|---|
| Time | Batch A ||| Viscosity (cP) |
| | D(v,0.1) | D(v,0.5) | D(v,0.9) | |
| 0m | 0.72 | 4.17 | 81.72 | 1634 |
| 3m | 0.75 | 4.18 | 89.06 | 1601 |
| 6m | 0.87 | 4.29 | 91.07 | 1645 |

| Time | Batch B ||| Viscosity (cP) |
|---|---|---|---|---|
| | D(v,0.1) | D(v,0.5) | D(v,0.9) | |
| 0m | 0.73 | 4.04 | 73.61 | 1712 |
| 3m | 0.91 | 4.18 | 81.37 | 1659 |
| 6m | 0.96 | 4.06 | 79.48 | 1575 |

| Time | Batch C ||| Viscosity (cP) |
|---|---|---|---|---|
| | D(v,0.1) | D(v,0.5) | D(v,0.9) | |
| 0m | 0.63 | 3.59 | 73.62 | 1561 |

| Quetiapine 25mg/5ml ||||
|---|---|---|---|
| Time | Batch A ||| Viscosity (cP) |
| | D(v,0.1) | D(v,0.5) | D(v,0.9) | |
| 0m | 0.64 | 3.47 | 71.41 | 1097 |
| 3m | 1.03 | 4.01 | 107.18 | 1139 |
| 6m | 0.92 | 3.39 | 55.81 | 1125 |

| Time | Batch B ||| Viscosity (cP) |
|---|---|---|---|---|
| | D(v,0.1) | D(v,0.5) | D(v,0.9) | |
| 0m | 0.45 | 1.95 | 65.37 | 1110 |

| Quetiapine 100mg/5ml ||||
|---|---|---|---|
| Time | Batch A ||| Viscosity (cP) |
| | D(v,0.1) | D(v,0.5) | D(v,0.9) | |
| 0m | 10.19 | 28.83 | 60.66 | 1343 |
| Time | Batch B ||| Viscosity (cP) |
| | D(v,0.1) | D(v,0.5) | D(v,0.9) | |
| 0m | 9.68 | 29.65 | 67.41 | 1388 |

Fig. 16B

| Batch | d(0.1) | d(0.5) | d(0.9) |
|---|---|---|---|
| 0001 | 10.232 | 28.823 | 60.306 |
| 0001 | 10.137 | 28.84 | 61.003 |
| 0002 | 9.742 | 30.043 | 69.495 |
| 0002 | 9.607 | 29.26 | 65.33 |
| 0003 | 19.008 | 51.032 | 112.038 |
| 0003 | 17.394 | 45.792 | 95.919 |
| 0004 | 9.378 | 27.49 | 61.811 |
| 0004 | 8.214 | 26.284 | 61.335 |
| 0005 | 7.977 | 28.969 | 82.749 |
| 0005 | 7.796 | 27.703 | 69.444 |
| 0006 | 3.666 | 29.285 | 71.918 |
| 0006 | 21.424 | 50.933 | 95.747 |

Fig. 16C

| 12.5 mg/5ml | Viscosity (cP) | 25 mg/5ml | Viscosity (cP) | 100 mg/5ml | Viscosity (cP) |
|---|---|---|---|---|---|
| Lot 1001 | 1624 | Lot 2001 | 905 | Lot 3001 | 1233 |
| Lot 1002 | 1287 | Lot 2002 | 832 | Lot 3002 | 1303 |
| Lot 1003 | 1390 | Lot 2003 | 928 | Lot 3003 | 1221 |
| Lot 1004 | 1172 | Lot 2004 | 790 | Lot 3004 | 1233 |
| Lot 1005 | 1460 | Lot 2005 | 941 | Lot 3005 | 1180 |
| Lot 1006 | 1460 | Lot 2006 | 881 | Lot 3006 | 1280 |
| Lot 1007 | 1505 | Lot 2007 | 982 | Lot 3007 | 1371 |
| Lot 1008 | 1052 | - | - | Lot 3008 | 1220 |
| - | - | - | - | Lot 3009 | 1259 |

Fig. 17

| Test Name | Parameter | Test value (T/R) | Lower 90% CI | Upper 90% CI |
|---|---|---|---|---|
| Classic 90% CI | $C_{max}$ | 109.713 | 98.809 | 121.821 |
| Classic 90% CI | $AUC_{0-T}$ | 106.711 | 97.917 | 116.295 |
| Classic 90% CI | $AUC_{0-INF}$ | 106.653 | 97.919 | 116.166 |

Fig. 18

| Parameter (unit) | Statistic | Oral suspension (20mg/mL) | Tablet (100mg) |
|---|---|---|---|
| Cmax (ng/mL) | Mean (SD) | 285.367 (114.174) | 265.383 (109.631) |
|  | CV | 40.009 | 41.310 |
| Tmax (hr) | Mean (SD) | 0.656 (0.280) | 1.000 (0.494) |
|  | CV | 42.635 | 49.355 |
| AUC0-t (ng/mL*hr) | Mean (SD) | 864.133 (513.452) | 791.019 (412.309) |
|  | CV | 59.418 | 52.124 |
| AUC0-inf (ng/mL*hr) | Mean (SD) | 874.378 (515.294) | 802.065 (417.794) |
|  | CV | 58.933 | 52.090 |
| AUC% extra (%) | Mean (SD) | 1.333 (0.555) | 1.387 (0.476) |
|  | CV | 41.647 | 34.282 |
| T1/2 (hr) | Mean (SD) | 4.906 (0.768) | 4.775 (0.839) |
|  | CV | 15.653 | 17.574 |
| MRT (1/hr) | Mean (SD) | 4.630 (0.818) | 4.786 (0.914) |
|  | CV | 17.672 | 19.098 |

AUC=area under the concentration-time curve; AUC0-inf=area under the curve from time 0 to finite; AUC0-t=area under the curve from time 0 until the last quantifiable point; Cmax=peak drug concentration; CV=coefficient of variation; MRT=mean residence time; SD=standard deviation; T1/2=plasma half-life; Tmax=time to peak drug concentration

ORAL QUETIAPINE SUSPENSION FORMULATIONS WITH EXTENDED SHELF LIFE AND ENHANCED BIOAVAILABILITY

FIELD OF THE INVENTION

The present invention is generally directed to novel suspension formulations of quetiapine fumarate for therapeutic oral administration having high bioavailability and extended physiochemical stability and to processes for preparing and administering such formulations.

BACKGROUND OF THE INVENTION

The invention generally relates to physicochemically stable pharmaceutical formulations for oral administration comprising an effective amount of quetiapine fumarate in a pharmaceutically acceptable, aqueous, suspension-stabilizing vehicle. The active pharmaceutical ingredient (API) quetiapine fumarate 2-[2-(4-dibenzo [b,f][1,4]thiazepin-11-yl-1-piperazinyl)ethoxy]-ethanol fumarate (2:1) is a well-known compound having anti-psychotic activity first marketed as a tablet under the brand name SEROQUEL™. Quetiapine fumarate has also been referenced as 11-[4-[2-(2-hydroxyethoxy)ethyl]piperazinyl]dibenzo[b,f][1,4] thiazepine and Bis[2-[2-[4-(dibenzo[b,f] [1,4]thiazepin-11-yl) piperazin-1-yl]ethoxy]ethanol](2E)-but-2-enedioate.
Further details about this compound are disclosed in the United States Pharmacopeial Convention Nov. 1, 2015 Revision Bulletin, the disclosure of which is hereby incorporated by way of reference. The preparation, physical properties and pharmacological properties of quetiapine fumarate are further described in published European Patents EP 240,228 and 282,236 as well as in U.S. Pat. No. 4,879,288, the entire contents of which are herein incorporated by reference.

Quetiapine fumarate is able to treat both the positive (hallucinations, delusions) and negative symptoms (emotional withdrawal, apathy) of psychosis and is associated with fewer neurological and endocrine related side effects compared to older agents. Quetiapine fumarate has also been associated with a reduction in hostility and aggression. Quetiapine fumarate is associated with fewer side effects such as EPS, acute dystonia, acute dyskinesia, as well as tardive dyskinesia. Quetiapine fumarate has also helped to, enhance patient compliance with treatment, ability to function and overall quality of life, while reducing recidivism (P. Weiden et al., Atypical antipsychotic drugs and long-term outcome in schizophrenia, 11 J. Clin. Psychiatry, 53-60, 57 (1996)). The enhanced tolerability profile of quetiapine is particularly advantageous in the treatment of patients hypersensitive to the adverse effects of antipsychotics (such as elderly patients).

Quetiapine fumarate has plasma half-life of 6 h and poor oral bioavailability due to extensive first-pass metabolism. Quetiapine tablets are available in different API strengths equivalent to 50 mg, 100 mg, 150 mg, 200 mg, 300 mg and 400 mg of quetiapine fumarate for oral administration up to twice a day. Other than the present invention disclosure, which was fully licensed for use in the UK on Jun. 20 2016, quetiapine fumarate is only marketed as a solid dosage formulation either under the brand name SEROQUEL™ or various bioequivalent generic solid dose formulations. Examples of extemporaneously compounded liquid quetiapine fumarate compositions made from solid tablets exist in the current literature, as do various unlicensed formulations in the UK, but they demonstrate elevated physiochemical instability (e.g., short shelf lives, degraded API, agglomeration, etc.) and uncertain bioavailability.

Various pharmaceutical forms are used for oral administration of drugs. In addition to solid single-dose forms such as tablets, hard and soft gelatin capsules, liquid forms such as solutions and syrups are also given, in which the dose to be administered can be adjusted by means of the volume given.

Individuals often require a high dose of quetiapine for therapeutic effect. For example a 400 mg tablet, administered twice times a day contains approximately 800 mg of quetiapine. For certain individuals, quetiapine fumarate can be prescribed at dosages higher than 800 mg/day. When such high doses of quetiapine are combined with excipients, the resulting oral solid dosage form (e.g., tablets) can be prohibitive both from a physical perspective (e.g., difficulty swallowing large tablets) and a chemical perspective (e.g., iatrogenic events resulting from elevated levels of excipients commonly used in solid oral dosage forms). Moreover, dose titration is difficult with fixed dose formulations. Dose titration is particularly relevant for neuropsychiatric medications where optimal therapeutic efficacy is often determined on an individual patient basis. Often, such optimal dosages (e.g., 190 mg) are not available in standard solid dose formulations.

Solid dose drug formulations also pose adherence problems. Medication adherence to solid dose drug formulations is particularly problematic in (i) elderly and pediatric patient populations with swallowing difficulties, (ii) patients who feign drug ingestion (i.e., "cheeking") and (iii) patients sensitive to drug excipients normally found in solid oral dose formulations. Solid dose formulations also exhibit a lag time from ingestion until therapeutic effects are observed. Liquid oral formulations generally demonstrate faster pharmacodynamics (e.g., $T_{max}$) than their solid dose counterpart. This is particularly important for individuals who are either agitated, rapidly escalating or actively experiencing a neuropsychiatric event. Thus, a clear need exists for alternative, non-solid oral formulations of quetiapine with high bioavailability and extended physiochemical stability.

Despite a market demand for alternative oral formulations, quetiapine fumarate is marketed only in solid dose formulations (e.g., SEROQUEL™ and generic solid dose equivalents). Other than the present invention, there are no known oral liquid quetiapine fumarate formulations approved as a prescription product. Efforts toward developing shelf-stable, oral liquid formulations of quetiapine fumarate have largely been thwarted by significant physiochemical challenges including low API solubility at physiologic pH and high chemical instability at low pH (i.e., increasing solubility decreases stability).

Lipid nanoparticle formulations of quetiapine fumarate have been disclosed, but demonstrate poor bioavailability and significant commercial manufacturing challenges. U.S. Pat. No. 6,716,416 describes aerosol formulations have been developed for the delivery of antipsychotics via inhalation, the disclosure of which is hereby incorporated by way of reference. US Pat. App. No. 20050158383 describes three alternative solid dosage forms of quetiapine hemifurate containing a wax material, press-coat dosage formulations, and controlled release formulations, the disclosure of which is hereby incorporated by way of reference. Shantaram, et. al teaches that hydrogel based nanocrystal formulations of quetiapine fumarate demonstrate moderate bioavailability, but are difficult to manufacture in a consistent and commercially affordable manner. Extemporaneously prepared quetiapine suspension formulations originating from compounding pharmacies generally demonstrate no more than thirty-day shelf stability and inconsistent bioavailability. U.S. Pat. No. 6,599,897 teaches away from stable oral quetiapine liquid suspension formulations and towards dissolvable quetiapine fumarate granules lacking suspending agents such as xanthan gum, the disclosure of which is hereby incorporated by way of reference.

The present invention generally describes novel oral liquid suspension quetiapine fumarate compositions of varying API concentrations having commercially relevant physiochemical stability and bioavailability generally bioequivalent to that of currently marketed solid dose formulations. An exhaustive written description of the disclosed invention is described at the Public Assessment Report (PAR) for Quetiapine Rosemont 20 mg/ml Oral Suspension (PL 00427/0240; UK/H/5869/001/DC), the entire contents of which are herein incorporated by reference. The present invention is the first and only known oral liquid formulation of quetiapine fumarate that has received regulatory approval as a prescription drug product.

For certain patient populations, the disclosed oral liquid formulations are a discernible improvement over (i) previously disclosed and commercially marketed solid oral dosage forms of quetiapine fumarate (i.e., SEROQUEL™), (ii) generic equivalent solid dosage formulations as well as (iii) extemporaneously compounded liquid formulations. The present invention also generally discloses methods of preparing such oral liquid quetiapine formulations as well as methods of treatment with oral liquid quetiapine formulations.

SUMMARY OF THE INVENTION

The present invention relates generally to physicochemical stable aqueous compositions comprising a pharmaceutically effective amount of quetiapine fumarate, pharmaceutically acceptable vehicle and a thickening agent in suspension. The present compositions contain quetiapine fumarate between about 2 mg/mL to about 40 mg/mL of quetiapine fumarate. More preferably the concentrations of quetiapine fumarate are about 12.5 mg/5 ml, 25 mg/5 ml, 100 mg/5 ml and 200 mg/5 ml (i.e., 2.5 mg/ml, 5 mg/ml, 20 mg/ml and 40 mg/ml, respectively). The most preferred compositions of the present invention contain approximately 20 mg/ml to 40 mg/ml quetiapine fumarate that remains physicochemically stable for at least twenty-four months. It will be apparent to those skilled in the art that such formulations can be co-administered with other therapeutic or prophylactic agents and/or medicaments that are not medically incompatible therewith.

The inventive oral composition has quetiapine fumarate in a suspension formulation and can optionally include, for example, at least one pharmaceutical excipient selected from a buffer, an antioxidant, a chelating agent, a preservative, a tonicity adjuster, a cyclodextrin, a surfactant, a suspending agent, a wetting agent, a stabilizer, a flocculating agent, a sweetener, a flavoring, a colorant, a cosolvent, and other ingredients. Oral liquid formulations can contain taste-masking ingredients such as sweeteners (artificial and/or natural) and flavorings.

The manufacture of the API used in the inventive composition is described in FIG. 1. The method summarizes the reaction of 11-piperazin-1-yldibenzo[b,f][1,4]thiazepine dihydrochloride with 2-(2-chloroethoxy) ethanol in toluene and N-methylpyrrolidone as solvents, at reflux temperature in the presence of a strong base (to afford the free base of the dibenzo derivative prior to the reaction) and sodium iodide (to obtain 2-(2-iodoethoxy) ethanol prior to the reaction, which is more reactive than the chloro derivative). Once the reaction is over, the quetiapine base obtained is reacted with fumaric acid to obtain the desired fumarate salt.

The inventive compositions generally have a pH of between about 5.0 to about 6.0 and are comprised according to FIG. 2. A preferred embodiment has a pH of between about 5.2 to about 5.8. The inventive compositions are manufactured according to FIG. 3 and the following:

Add Purified Water (A) to the main vessel.
Add the Citric Acid Monohydrate to the main vessel and mix until dissolved using a high-shear mixer.
Add the Disodium Hydrogen Phosphate Dihydrate to the main vessel and mix until dissolved using a high-shear mixer.
Add Sucralose to the main vessel and mix until dissolved using a high-shear mixer.
Add the Simethicone Emulsion (Q7-2587 30%) to the main vessel and mix until dispersed using a high-shear mixer.
Add Quetiapine Fumarate to the main vessel and mix using a high-shear mixer until a homogeneous suspension is produced.
To a separate stage vessel add the Propylene Glycol.
To the separate stage vessel add Methyl Hydroxybenzoate
To the separate stage vessel add Propyl Hydroxybenzoate and mix using a high-shear mixer until dissolved.
To the preservative solution in the separate stage vessel add Xanthan Gum and mix until homogenous using a propeller mixer.
Add the preservative solution/Xanthan Gum slurry in the separate stage vessel to the main vessel and mix using a high-shear mixer until a uniformly thickened suspension is produced.
Add the Lemon Flavour to the main vessel and mix with a high-shear mixer until dispersed.
Check the pH of the solution (target pH is 5.50). If the pH is outside the range of 5.2-5.8 adjust the pH until it within this range by using either 10% w/v Citric Acid Monohydrate solution to lower pH or a 10% w/v Disodium Hydrogen Phosphate Dihydrate solution to increase the pH.
Add Purified Water (B) to make to final volume and mix until dispersed using a high-shear mixer.
Fill 152±2 ml of finished product into 180 ml amber glass bottles and close with child resistant closures.

The basic principle of manufacture of the bulk drug suspension product is the use of stainless steel mixers in stainless steel 316 pharmaceutical grade vessels to suspend ingredients in suspending agents until a homogeneous suspension is obtained. The following is a list of essential equipment: 100 L Stainless steel tank; Medium high shear mixer (50 L-200 L); Bench top high shear mixer (<10 L); Bench top air driven propeller mixer (<10 L); Mobile electric propeller mixer (50 L-400 L). Critical intermediates of the inventive composition can be monitored and controlled according to the in-process control limits described in FIG. 4.

The inventive formulation may be used to treat a patient in need of an effective amount of quetiapine fumarate. The present invention further provides methods of treating at least one symptom or condition associated with but not limited to:

1) Schizophrenia and other Psychotic Disorders including but not limited to Psychotic Disorder, Schizophreniform Disorder, Schizoaffective Disorder, Delusional Disorder, Brief Psychotic Disorder, Shared Psychotic Disorder, and Psychotic Disorder Due to a General Medical Condition;
2) Dementia and other Cognitive Disorders;
3) Anxiety Disorders including but not limited to Panic Disorder Without Agoraphobia, Panic Disorder With Agoraphobia, Agoraphobia Without History of Panic Disorder, Specific Phobia, Social Phobia, Obsessive-Compulsive Disorder, Post Traumatic Stress Disorder, Acute Stress Disorder, Generalized Anxiety Disorder and Generalized Anxiety Disorder Due to a General Medical Condition;
4) Mood Disorders including but not limited to a) Depressive Disorders, including but not limited to Major Depressive Disorder and Dysthymic Disorder and b) Bipolar Depression and/or Bipolar mania including but not limited to Bipolar I Disorder, including but not limited to those with manic, depressive or mixed episodes, and Bipolar n Disorder, c) Cyclothymic Disorder, d) Mood Disorder Due to a General Medical Condition;
5) Sleep Disorders;
6) Disorders Usually First Diagnosed in Infancy, Childhood, or Adolescence including but not limited to Mental Retardation, Learning Disorders, Motor Skills Disorder, Communication Disorders, Pervasive Developmental Disorders, Attention-Deficit and Disruptive Behavior Disorders, Feeding and Eating Disorders of Infancy or Early Childhood, Tic Disorders, and Elimination Disorders;
7) Substance-Related Disorders including but not limited to Substance Dependence, Substance Abuse, Substance Intoxication, Substance Withdrawal, Alcohol-Related Disorders, Amphetamine (or Amphetamine-Like)-Related Disorders, Caffeine-Related Disorders, Cannabis-Related Disorders, Cocaine-Related Disorders, Hallucinogen-Related Disorders, Inhalant-Related Disorders, Nicotine-Related Disorders, Opioid-Related Disorders, Phencyclidine (or Phencyclidine-Like)-Related Disorders, and Sedative-, Hypnotic- or Anxiolytic-Related Disorders;
8) Attention-Deficit and Disruptive Behavior Disorders;
9) Eating Disorders;
10) Personality Disorders including but not limited to Obsessive-Compulsive Personality Disorder; and
11) Impulse-Control Disorders, comprising administering to a mammal a therapeutically effective amount of a formulation of the invention.

Other medical indications known to be responsive to quetiapine fumarate treatment are within the scope of this invention.

BRIEF DESCRIPTION OF THE DRAWINGS

FIG. 2 shows the excipient concentrations (% w/v) for finished product strengths of quetiapine fumarate.
FIG. 4 shows the control of critical steps and intermediates.
FIG. 6 shows API Stability. 10 mg/mL solutions of each batch of Quetiapine Fumarate were prepared in 65:35 acetonitrile:water diluent. 5 mL of each of these solutions were degraded according to the following conditions: Control (non-degraded sample solution); Heat (Refluxed for 2 hours with 5 mL of purified water); Metal (Refluxed for 2 hours with 5 mL of a solution containing 10 ppm Fe ions); Base (Refluxed for 2 hours with 5 mL of 1M sodium hydroxide); Acid (Refluxed for 2 hours with 5 mL of 1M hydrochloric acid); Peroxide (Refluxed for 2 hours with 5 mL of 0.5 vol hydrogen peroxide). Following reflux, the samples were cooled, transferred to volumetric flasks and diluted to 50 mL with 65:35 acetonitrile:water diluent.

FIG. 7 shows the API starting particle diameter, dissolution recovery, and agglomeration.
FIG. 8 shows finished product prepared with API of varied particle size.
FIG. 9A shows dissolution of 100 mg/5 mL samples prepared with varied particle size drug substance (pH6.8 media).
FIG. 11 shows quetiapine fumarate polymorphic forms.
FIG. 14 shows XRPD peaks of quetiapine fumarate: API and suspensions versus literature values.
FIG. 15 shows finished product maximum daily excipient levels.
FIG. 16A shows particle size and viscosity data for production scale batches.
FIG. 16B shows particle size for additional production scale batches.
FIG. 16C shows viscosity data for additional production scale batches.
FIG. 17 shows 90% confidence intervals for quetiapine mean test/reference ratios.
FIG. 18 shows pharmacokinetic parameters of oral quetiapine fumarate suspension vs. tablet.

DETAILED DESCRIPTION OF THE INVENTION

Figure 1:
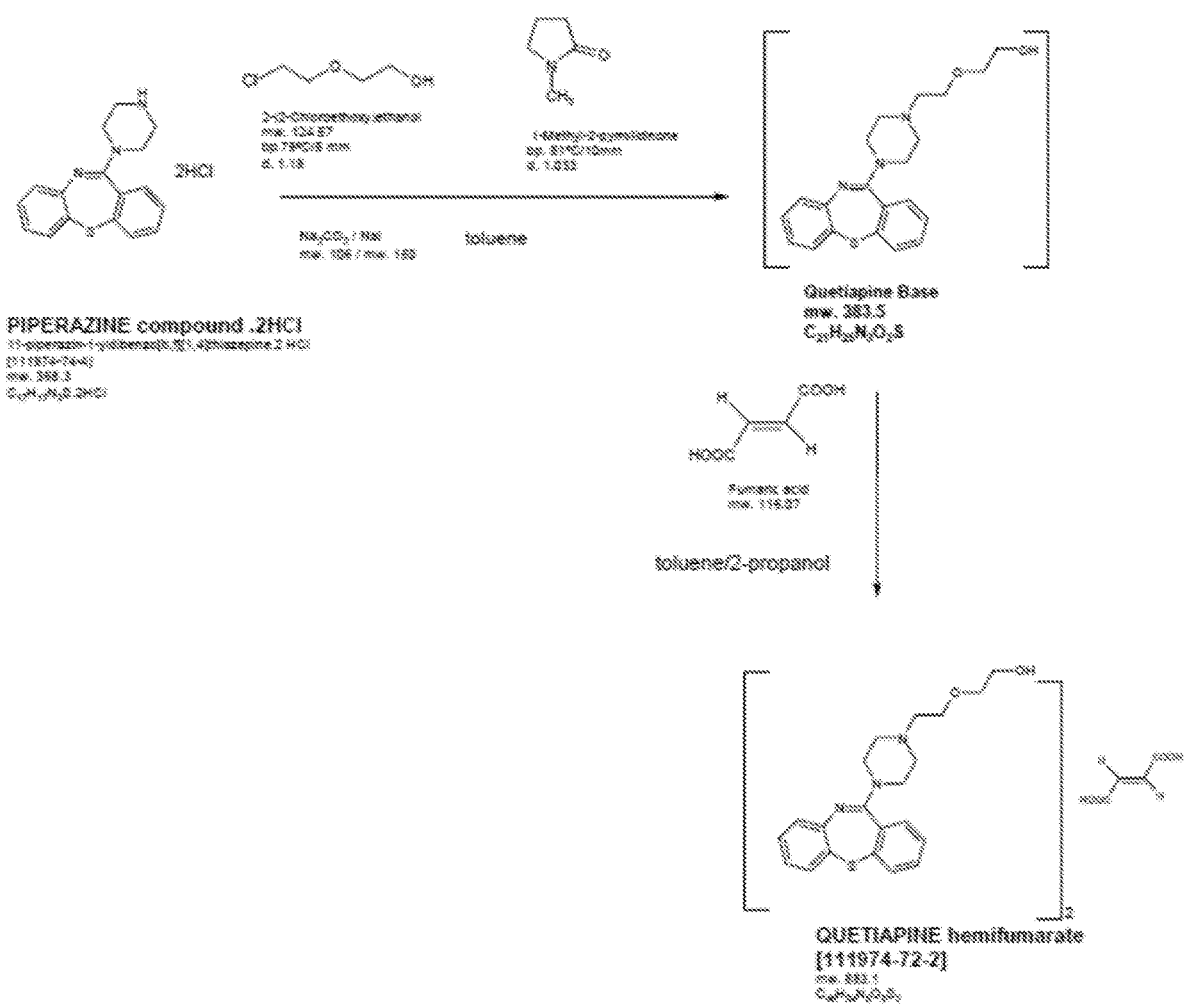
FIG. 1 shows the API manufacturing process.
Figure 3:
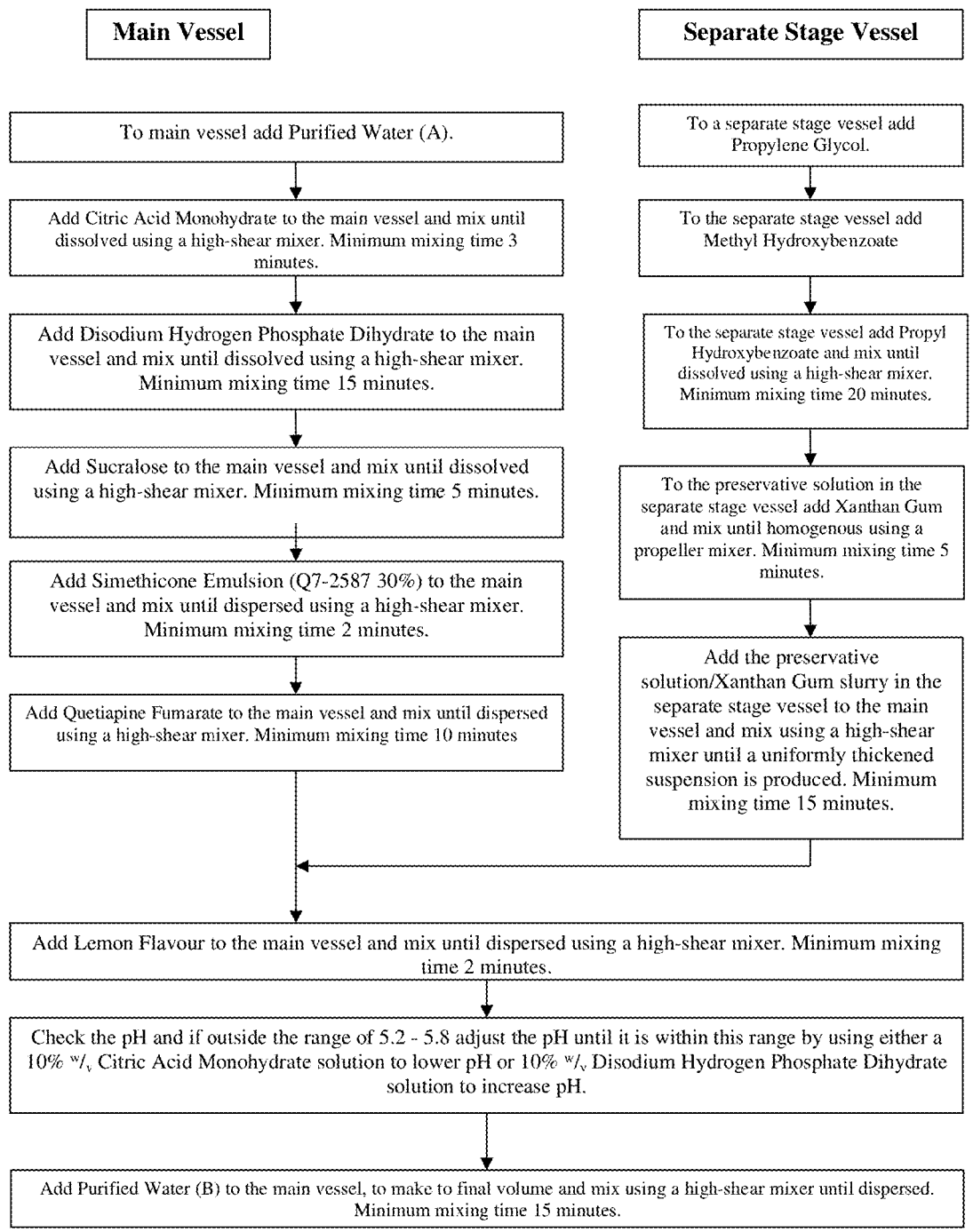
FIG. 3 shows the manufacturing process of quetiapine fumarate oral suspension.

To date, the only U.S. approved formulations of quetiapine fumarate are solid dosages (e.g., SEROQUEL™ and their generic equivalents). For example, U.S. Pat. No. 7,959,948 describes a solid dosage extended release quetiapine fumarate pharmaceutical composition comprising (i) quetiapine or a pharmaceutically acceptable salt thereof (ii) a mixed excipient comprising an intimate admixture of polyvinylacetate and polyvinylpyrrolidone in a weight ratio from 5:2 to 10:2; and, optionally (iii) an acid, especially fumaric acid. U.S. Pat. No. 6,214,286 describes prompt-release oral pharmaceutical compositions for the creation of "ready-to-use" extemporaneous suspensions where the active agent is in microgranule form coated with a lipid film coating mixture. U.S. Pat. No. 7,794,750 describes solid dose, controlled-release formulations of quetiapine. U.S. Pat. App. No. 2007/0031340 describes an aerosol producing drug delivery device and thin-film formulation of quetiapine. U.S. Pat. No. 5,156,842 describes a non-aqueous pharmaceutical liquid suspension for oral administration comprising an API suspended in an edible, non-aqueous carrier vehicle (e.g., mineral oil) in the form of controlled release particles. U.S. Pat. No. 6,599,897 discloses dissolvable quetiapine fumarate granules lacking suspending agents. The entire contents of the above U.S. patent and patent applications are herein incorporated by reference.

Medication compliance is an essential component of successful treatment for neuropsychiatric disorders. Medication adherence to solid dose drug formulations is particularly problematic in (i) elderly and pediatric patient populations with swallowing difficulties, (ii) patients who feign drug ingestion (i.e., "cheeking") and (iii) patients who are sensitive to drug excipients normally found in solid dose formulations.

Possible solutions for enhancing solid dose medication compliance would be the development of physicochemically stable bioequivalent oral liquid formulations (e.g., solutions, emulsions, suspensions, and syrups with long shelf lives). Relative to solid dose formulations, oral liquid formulations are easier to swallow, demonstrate faster absorption kinetics, and are easier to titrate on a per patient basis. Other possible solutions could include the development of easier to swallow tablets, capsules, sustained release formulations, transdermal patches, suppositories, lozenges, parenteral formulations, ocular formulations, inhalation formulations, sublingual tablets, topical formulations (e.g., creams, ointments, gels, pastes, lotions, powders), and/or easily reconstituted lyophilized formulations.

For patients who have difficulty in swallowing, feign ingestion, are children or are seeking alternatives to oral solid dosage forms, pharmacies are often forced to individually compound liquid formulations using crushed quetiapine. Such extemporaneously created suspensions of quetiapine fumarate are problematic in part because they are not physicochemically stable (e.g., over time the active agent settles out of the compounded formulation or is degraded) leading to highly variable API dosing with accompanying unpredictable therapeutic efficacy. The failure of others to develop a liquid oral quetiapine formulation, despite a commercial demand, suggests that while those of ordinary skill in the art may have already attempted to develop such oral liquid drug suspensions, extensive physiochemical barriers preclude a reasonable expectation of success. Indeed, U.S. Pat. No. 8,057,811 highlights the difficulties of formulating aqueous suspensions of a related anti-psychotic, clozapine, and is hereby incorporated by reference.

A buffer or buffer system can be optionally added to the liquid, for example, to maintain pH in a desired range, retain antimicrobial activity or enhance the solubility of the pharmaceutically active agent. Suitable buffers are those that are not chemically reactive with other ingredients and are present in amounts sufficient to provide the desired degree of pH buffering. In some embodiments, the buffer is selected to assist in maintaining a slightly acidic pH of the liquid formulation and to balance electrical charges among API, suspending agents, and excipients allowing for optimal drug performance characteristics. In a preferred embodiment, the buffer is a buffer system comprising a buffer pair of citric acid monohydrate and di-sodium hydrogen phosphate dihydrate.

Figure 5:
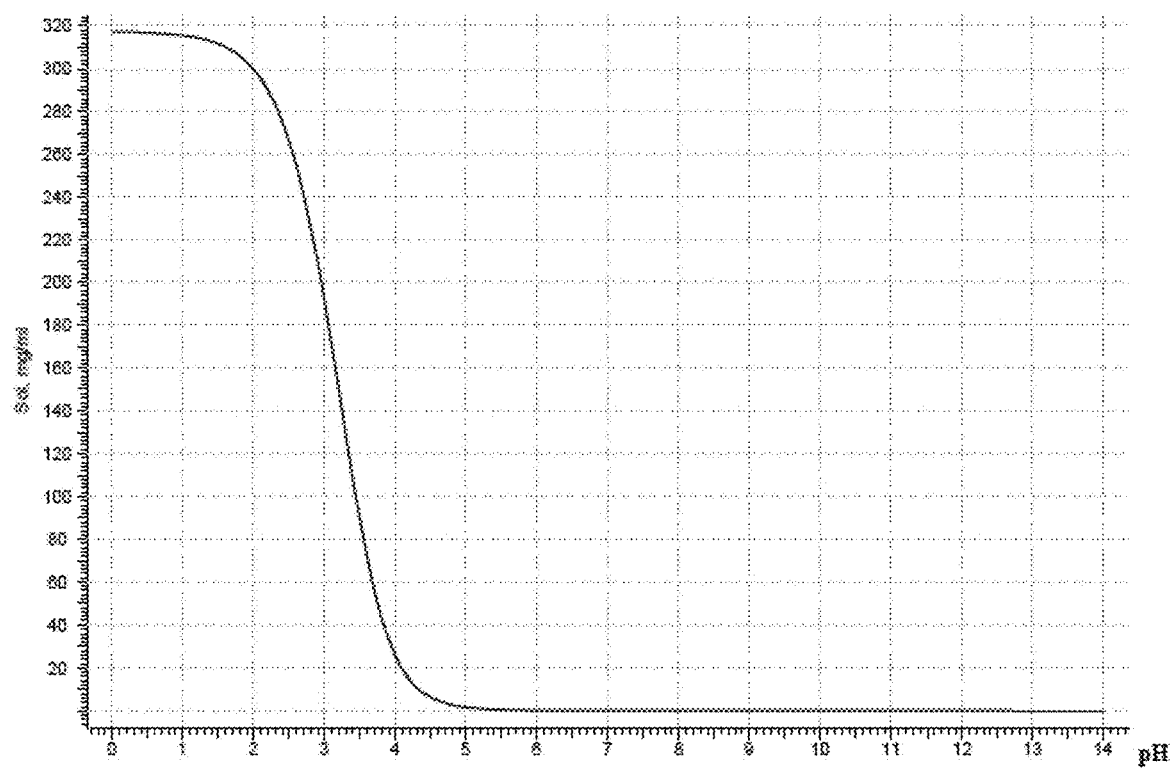
FIG. 5 shows the solubility chart for quetiapine fumarate.

Quetiapine fumarate is a weak acid with dissociation constant (pKa) 3.3 and 6.8 with moderate pH dependent solubility, 94.3 mg/ml to 2.37 mg/ml at pH values from 1 to 9 reported. At lower pH, where quetiapine is very soluble (1.499 g/5 ml at pH2 and 952.1 mg/5 ml at pH3), acidic solutions tend to promote API degradation as well as impart undesirable acidic taste. As pH increases, the solubility of quetiapine fumarate rapidly decreases FIG. 5. This application discloses the first example of an aqueous suspension of quetiapine fumarate with extended physicochemical stability and therapeutic bioavailability equivalent to that of commercially approved solid dose formulations.

Liquid oral drug suspension formulations are far more complex and unpredictable than their fully soluble liquid formulation counterparts. For drugs with low solubility and/or bioavailability at physiological pH, efforts to develop suspension formulations are often met with varying rates of success due to restrictive physiochemical parameters of the API and/or excipients. While simply increasing the volume of diluent for low-solubility drugs may lead to improved solubility, the large volume of diluent is often prohibitive from a patient perspective. Formulations in which the drug is solubilized using a co-solvent(s) often demonstrate unforeseeable precipitation and/or phase separation during long-term storage. Finally, as is the case for quetiapine fumarate, forcing an API into solution often requires conditions (e.g., pH<3.5) well out of the range of acceptable oral tolerability.

Therapeutically effective quetiapine suspensions are particularly problematic since the API and subsequent oral suspension formulations must not only exhibit high bioavailability, but also high physicochemical stability. FIG. 6 discloses the chemical stability of four commercial lots of the API. While we hypothesized that API degradants or impurities could contribute to formulation difficulties, we observed no substantive differences among all API sources.

The necessity for drug products to have extended shelf lives (e.g., longer than 12 months) is highlighted by the retail pharmacy practice of routinely returning drug products (including neuropsychiatric drugs) with remaining shelf lives of less than twelve months. While drugs in suspensions are generally chemically more stable than in fully soluble solutions, the chemical stability often comes at the expense of unpredictable physical instability—drug suspensions tend to settle, phase separate, marble and/or agglomerate upon storage leading to unacceptably high variations in dosing. FIG. 7 describes the API starting particle diameter, dissolution recoveries, and agglomeration of eight different development batches of product using API provided by four different source manufacturers.

Figure 9B:
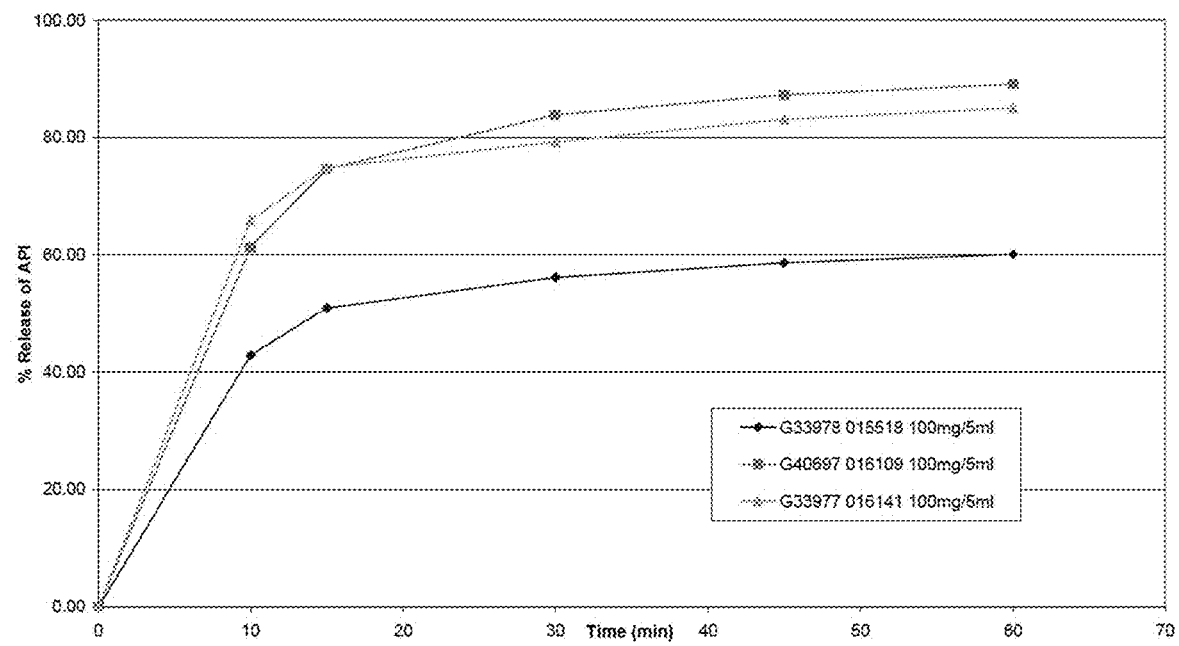
FIG. 9B shows the effect of particle size on dissolution rate in quetiapine oral suspensions.

The size and relative distribution of particle sizes of the drug substance was recognized as a critical component during the development process. A preferred embodiment of the invention will include quetiapine fumarate with a relative particle size distribution D (v, 0.9) between 30 μm and 60 μm. FIG. 8 describes 100 mg/5 ml suspensions produced with API of various particle sizes during the development process. FIG. 9a and FIG. 9b describe the dissolution profiles of the 100 mg/5 ml suspensions at pH 6.8.

Highlighting the unpredictability of developing a liquid suspension of quetiapine fumarate capable of retaining physicochemical stability, only one of four formulation concentrations (i.e., 20 mg/ml) had sufficient physicochemical shelf stability (i.e., 24 months), acceptable bioavailability (i.e., equivalent to the approved solid dose SEROQUEL™ formulation) and contained levels of excipients that were deemed safe for human exposure such that it could receive regulatory marketing approval (See MHRA, Procedure No: UK/H/5869/001/DC and UK License No: PL 00427/0240).

The rate of sedimentation of a suspended phase can be estimated by Stoke's equation (i.e., $V=d^2 (\rho 1-\rho 2)g/18 \eta o$). While a useful starting point, this equation assumes that (i) all dispersed particles are of uniform shape and size and (ii) that the particles are sufficiently far apart so that the movement of one does not affect the neighboring particles. Moreover, the Stokes' equation does not consider all the additional variables affecting the stability of a suspension, including but not limited to, particle size and purity of both API and excipients, storage temperature, electrical charge of API and excipients, concentration of suspending agent, use of surfactants and wetting agents, antifoaming agents, cosolvents, pH adjusting buffer systems, antimicrobial preservatives and physiochemical compatibility with packaging materials (e.g., plastics, glass, rubber).

While drug suspensions can facilitate chemical stability, drug suspensions often exhibit detrimental physical instability due, in part, to unpredictable particle-particle interactions (e.g., caking and/or compaction of API and/or excipients) as well as complex particle-aqueous solution interactions. Settling and aggregation often result in drug formulations that are difficult to resuspend and/or are susceptible to phase separation leading to variable dose administration.

Ideal drug suspension formulations are pseudoplastic—demonstrating high viscosity at low shear rates (e.g., during shelf storage) and low viscosity at high shear rates (e.g., during shaking and pouring). Pseudoplastic suspending agents (as well as thixotropic agents) are desirable, since they recover slowly from the deformation that occurs through shearing (i.e., upon shaking, they remain fluid long enough to be poured). We observe pseudoplasticity in the 20 mg/ml quetiapine fumarate formulation. Preferred compositions will retain a viscosity range of between 700-2000 cP at 25 degrees centigrade over the shelf life of the product.

While controlled flocculation has been shown to prevent caking (Sucker H., Fuchs P., Speiser P., Pharmazeutische Technologie, 5th Edition 1991, Georg Thieme Verlag, Stuttgart, p. 423), the commercial manufacture of stable suspensions by controlled flocculation is subject to limitations, since it is difficult to reproduce the optimum properties of suspension systems owing to the variability of the suspended solid and the stability of the excipients.

Figure 10:
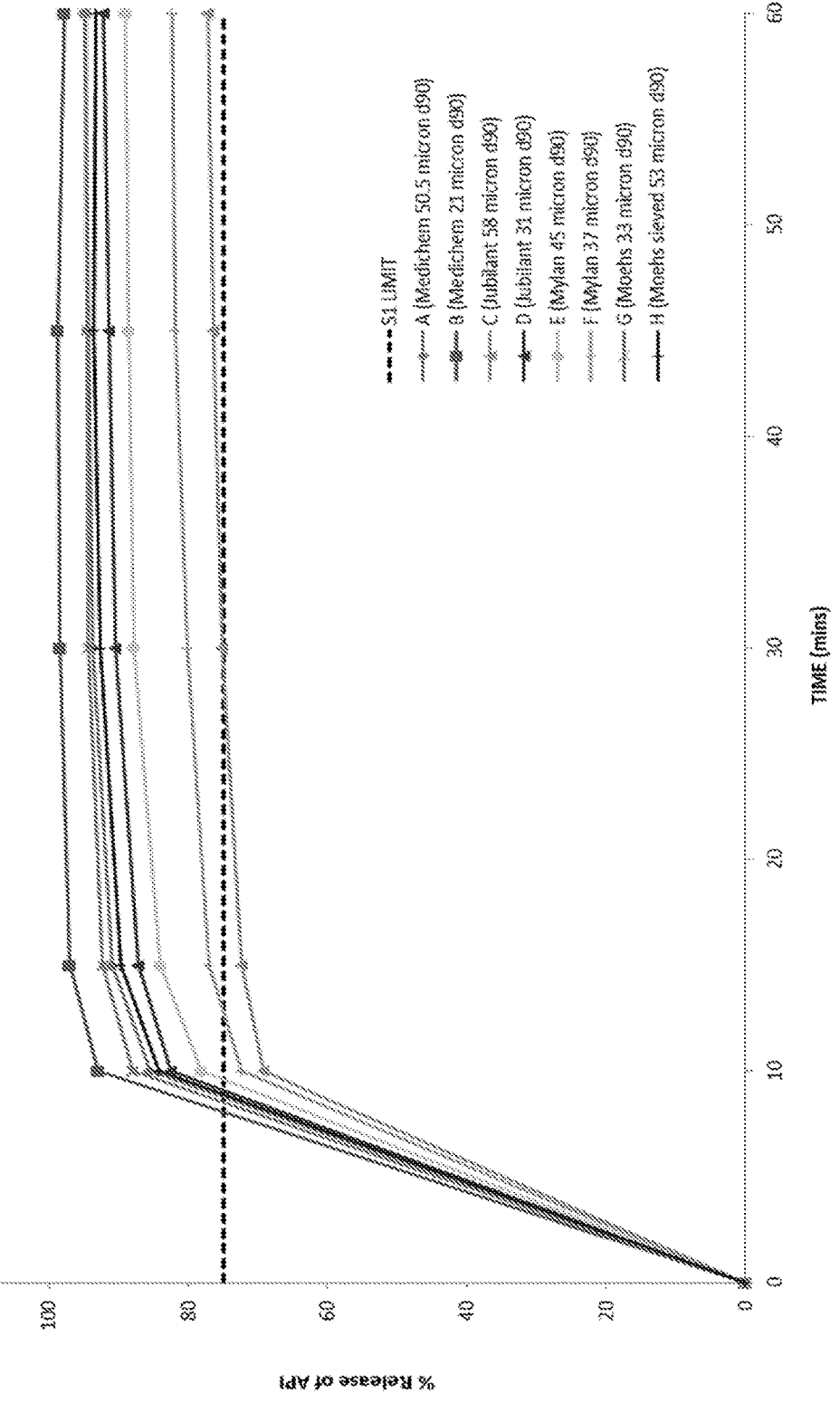
FIG. 10 shows quetiapine batch dissolution profiles.

Another potential source of physiochemical instability in suspension drug formulations lies in the source manufacturer of the API. For unknown reasons, batches of quetiapine fumarate produced with comparable laboratory specifications (e.g., USP grade drug substance with varying particle size controls) demonstrated surprisingly disparate physiochemical behavior when in suspension (compare FIG. 7, columns 2, 4 and FIG. 10). For clarity, FIG. 7 shows that suspensions produced with drug substance from manufacturers B and D show significant agglomeration in suspension at release, whereas suspensions produced with drug substance from manufacturers A and C do not. FIG. 10 highlights the variability in batch dissolution profiles of final oral suspension product made from various API sources.

The consistency of the physiochemical characteristics of the disclosed oral suspensions are typically influenced by a large number of variables, for example; the density of the internal and external phases; the ratio of the phase volumes; the viscosity of the external phase; and the dimensions, degree of aggregation, and shape of the particles. The variability of these parameters can cause difficulties during the development of the suspension, even after agitation at the time of use. In some cases, the difficulties lead to a nonhomogeneous distribution of the active agent.

Agglomeration is often an unpredictable physiochemical problem when developing drug suspension products. Agglomeration can modify the micrometric properties of pharmaceutical powders (e.g., flowability, packability and solubility) in unforeseen ways. Agglomeration can also influence phase segregation during processing and affect product bioavailability. Yari, et al. describes difficulties in understanding and reproducibly controlling process parameters governing agglomeration, the entire contents of which are herein incorporated by reference. In particular, Yari describes the uncertainties of how agglomerates form and evolve during the drug suspension manufacturing process using carbamazepine as a model API. Results show that agitation can influence the shape of the agglomerated particles in an unpredictable manner and that agglomeration of large crystals is often more difficult if they are elongated in shape. Smaller crystals on the other hand give rise to more spherical and larger agglomerates with smoother surface and denser structure.

Since there is no information in the art that would explain the difference in performance of comparable quetiapine fumarate API, and without being bound to any particular theory, we propose that an as yet uncharacterized physiochemical property related to the starting material (e.g., particle size, particle shape and/or trace polymorphisms) contributed, at least in part, to the inability of others to successfully develop a commercially viable, physicochemically stable liquid oral quetiapine formulation. Mentioned earlier, the present invention is the first and only known example of a liquid oral quetiapine product that has received regulatory approval for use as a licensed prescription product.

If necessary, the physical stability of drug suspensions can be controlled by the addition of flocculating agents to enhance particle dispersion and/or the addition of viscosity enhancers to reduce sedimentation rate in the flocculated suspension. While viscosity enhancers typically range from 0.5% to 5% of the final formulation, the ideal viscosity largely depends on a particle's unique chemistry and tendency to settle. Non-limiting examples of flocculating agents include, but are not limited to, electrolytes (e.g., KCL, NaCl), sulfates, citrates, phosphate salts, pH adjusting agents, alum, aluminium chlorohydrate, aluminium sulfate, calcium oxide, calcium hydroxide, iron (II) sulfate (ferrous sulfate), iron (III) chloride (ferric chloride), polyacrylamide, polyDADMAC, sodium aluminate, sodium silicate, chitosan, isinglass, moringa oleifera seeds, gelatin, strychnos potatorum seeds, guar gum, and alginates.

A suspension system was next explored as a means to limit physical instability of the inventive composition while maintaining high bioavailability. Exemplary suspending agents include: acacia, tragacanth, xanthan gum, carbomer, alginates, carrageenan, locust bean gum, guar gum, gelatin, methylcellulose, hydroxymethylcellulose, hydroxypropylmethylcellulose, microcrystalline cellulose, powdered cellulose, hydroxy ethylcellulose, sodium carboxymethylcellulose (CMC), and synthetic hydrocolloids such as Carbopol™. Bentonite, Hectorite, attapulgite, and Veegum K have also been used as suspending agents with mixed success.

After several suspending agents, and combinations thereof, were shown to adsorb quetiapine fumarate, it was determined that xantham gum by itself could be a viable suspending agent. While xantham gum demonstrated >99% recovery, after 2 weeks storage, the 20 mg/ml product began to settle and phase separate. Increasing xantham gum concentration up to and including 50% failed to correct the physiochemical instability of the 20 mg/ml product. Surprisingly, when the concentration of the citrate: phosphate buffer was doubled the inventive product became fully stabilized. In an embodiment, 0.4% w/v xantham gum was adequate to suspend quetiapine fumarate fumarate for an extended shelf stability at API loadings from 12.5 mg/5 ml to 200 mg/5 ml with citrate phosphate ranges from 0.9-1.8% w/v and disodium hydrogen phosphate ranges from 2.0-4.0% w/v Another potential source of unpredictability in suspension drug formulation development lies in the existence of chemical polymorphism. Many pharmaceutical compounds can crystallize with more than one type of molecular packing structure and/or with more than one type of internal crystal lattice. This phenomenon of identical chemical structure but different internal structure is generally referred to as polymorphism. Species having different molecular structures are referred to as polymorphs. Many pharmacologically active organic compounds can also crystallize such that a second, foreign molecule(s), especially solvent molecules, are regularly incorporated into the crystal structure of the principal pharmacologically active compound. This phenomenon is referred to as pseudopolymorphism and the resulting structures as pseudopolymorphs. When the second molecule is a solvent molecule, the pseudopolymorphs can be referred to as solvates. An important solid-state property of a pharmaceutical compound that can vary among polymorphs is its rate of dissolution in aqueous media (e.g., gastric fluid) and thus bioavailability. For a general review of polymorphs and the pharmaceutical applications of polymorphs see G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), which is incorporated herein by reference.

Figure 12:
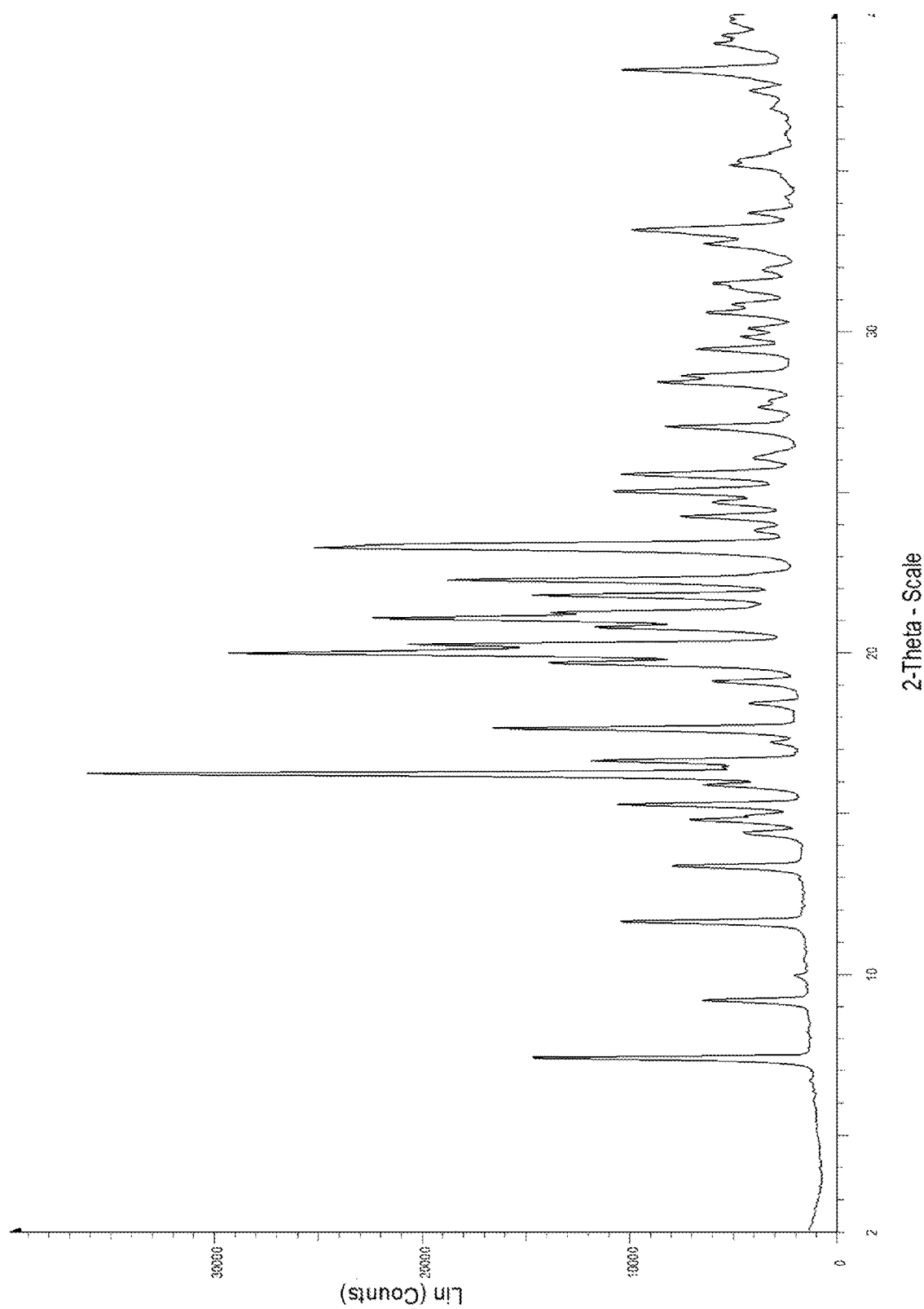
FIG. 12 shows XRPD Analysis of starting API.
Figure 13:
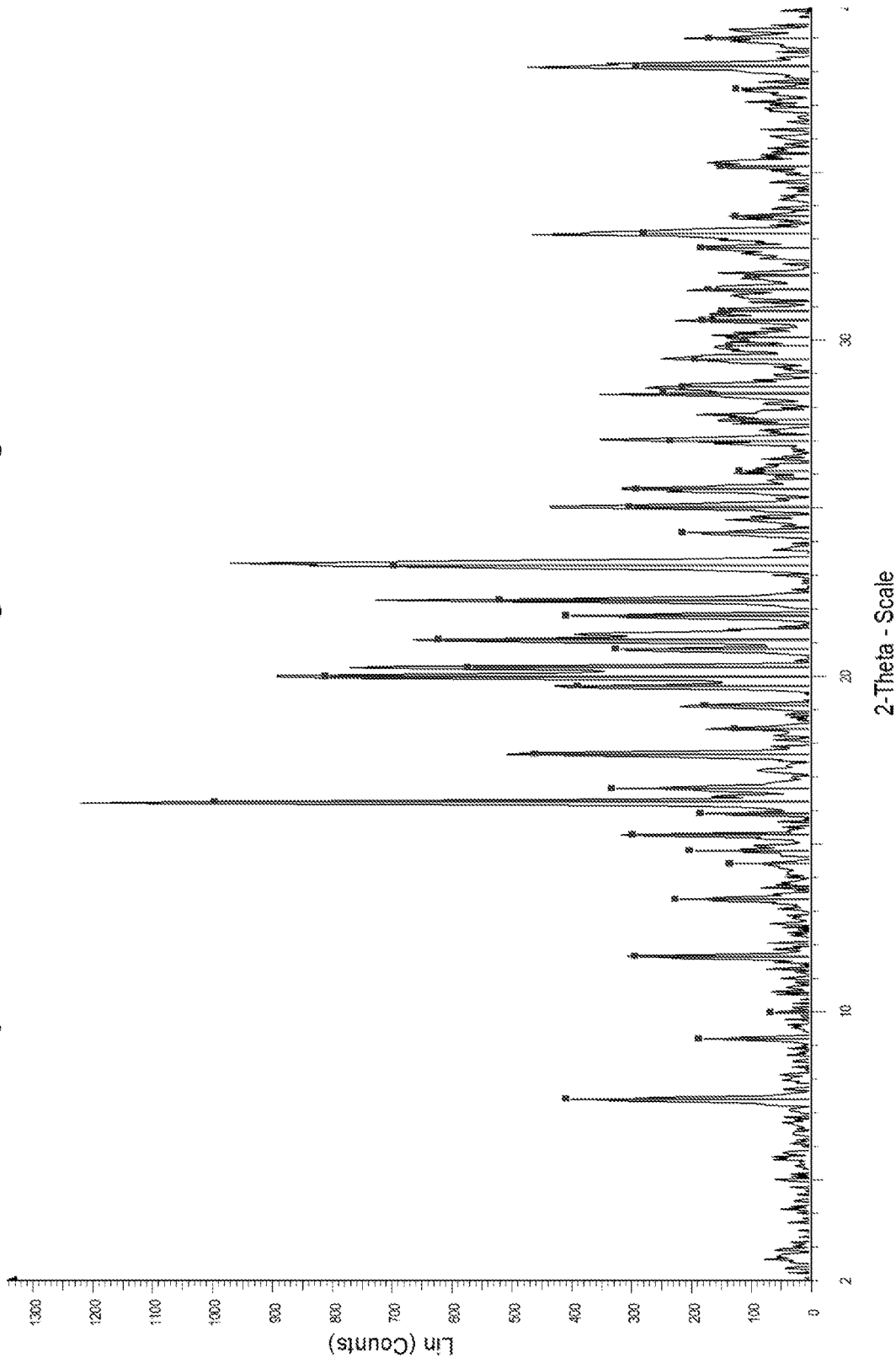
FIG. 13 shows representative XRPD analysis of liquid quetiapine suspensions.
Figure 13:
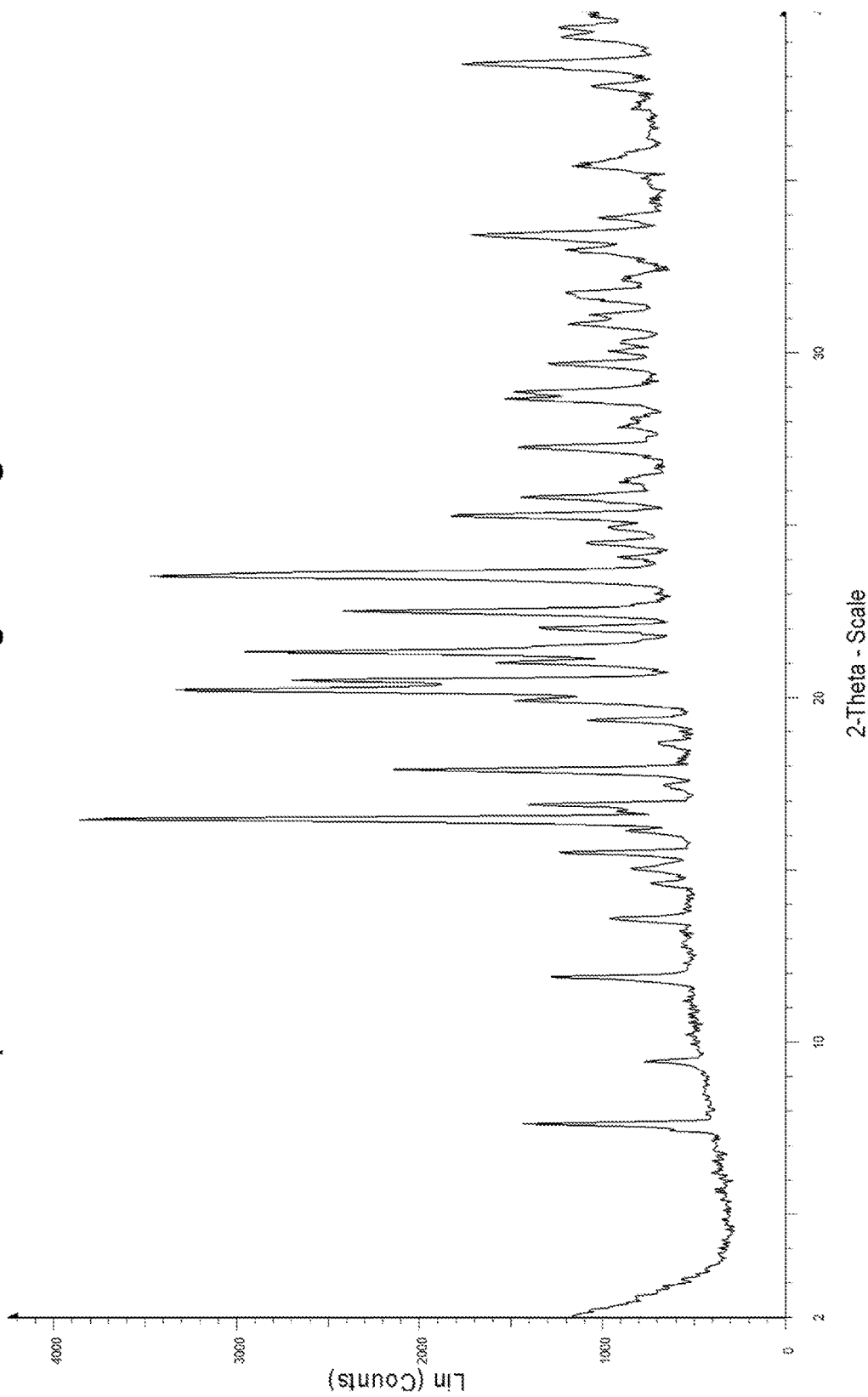
Figure 13:
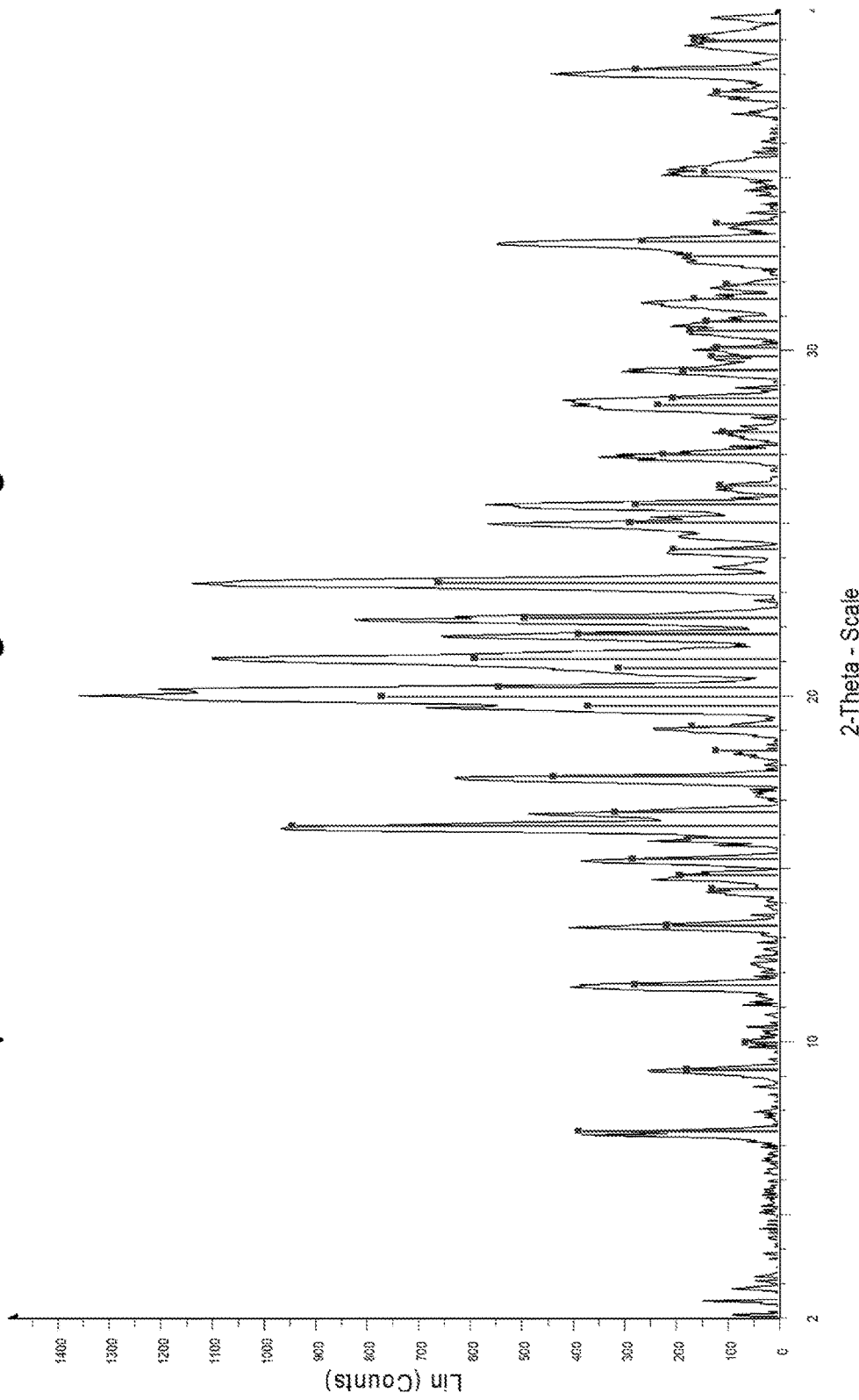

Quetiapine fumarate is known to exhibit polymorphism (FIG. 11). We investigated if polymorphism could be responsible for the failure of others to develop an oral liquid suspension of quetiapine fumarate. Powder X-Ray diffraction was carried out on a Bruker-AXS D8 Advance XRPD machine using 9 mm & 25 mm cavity PMMA sample holders. Manufacturer's API was loaded into 25 mm sample reception PMMA holder and analyzed from 2-40° 2theta (0.04° 2theta step size and 0.2 second dwell time—Agenda1 "Routine" conditions, Slits V20, using the LynxEye™ detector). Polymorphic analysis of all API manufacturing sources suggested that quetiapine fumarate to be generally of Form 1 (FIG. 12). Subsequent XRPD analysis of the inventive oral formulations similarly identified quetiapine fumarate in suspension as Form 1 suggesting that polymorphism did not change once API was suspended as an aqueous formulation (FIG. 13.)

All of the XRPD peaks present in the inventive formulations were attributable to API. No other API polymorphs were detected and no formulation excipients were seen in crystalline form. Diffraction patterns of the four suspension formulations (12.5 mg/5 ml, 25 mg/5 ml, 100 mg/5 ml, 200 mg/5 ml) of different time points were seen to be essentially identical, strongly suggesting that the API component is not changing polymorphic form during shelf storage. It is worth noting that the XRPD pattern for quetiapine fumarate is quite complex. Only the strongest peaks were characterized (>30% intensity). Not wishing to be bound by theory, it is possible that other polymorph contaminants exist may contribute to the physiochemical stability and/or bioavailability of the disclosed invention. The XRPD pattern observed for the starting API is significantly sharper than those obtained for the oral suspensions, the latter demonstrating a more amorphous pattern. As such, the peak positions for the oral suspensions may not be as precise as those for the starting API.

The manufacturing process for the quetiapine fumarate suspension drug product required use of a high shear mixer to hydrate the suspending agent and ensure efficient dispersion of the active. This in turn aerates the product and produces excessive foam on the surface of the product. It was determined that the use of an antifoaming agent was likely necessary. A variety of antifoaming agents exist, including: oil based defoamers (e.g., ethylene bis stearamide (EBS), paraffin waxes, ester waxes and fatty alcohol waxes), powder defoamers (e.g., silica), water based defoamers (e.g., mineral oil, vegetable oil, long chain fatty alcohol, fatty acid soaps or esters), silicone based defoamers (e.g., Polydimethylsiloxane), EO/PO based defoamers (e.g., polyethylene glycol and polypropylene glycol copolymers) and alkyl polyacrylates. Simethicone emulsion was ultimately found to be compatible with the API (and excipients) and able to ensure a suspension product that did not separate for at least a twenty-four month shelf life.

It is preferable that solid API particles distribute homogeneously in the suspension to ensure accurate and reproducible dosing. Unfortunately, solid particles of suspension are not easily wetted by water due to their hydrophobic nature. Some wetting agent, acting as surfactants, accomplish this by reducing the interfacial tension between the solid particle and the liquid medium. Surfactants have disadvantages in that (i) they have foaming tendencies, (ii) are bitter in taste, and (ii) interact with preservatives (e.g., methyl paraben) and reduce antimicrobial activity. Surfactants can generally include: polymeric surfactants, anionic surfactants cationic surfactants, non-ionic surfactants and amphoteric surfactants. Non-limiting specific examples can include sodium lauryl sulfate, glyceryl laurate, polyoxamers and benzalkonium chloride. Surprisingly, the disclosed invention did not require surfactants to ensure uniform particle distribution and consistent API dosing.

Pharmaceutical excipients are pharmaceutically acceptable ingredients that are essential constituents of virtually all pharmaceutical products. The inventive pharmaceutical suspensions may comprise at least one additional component selected from the group consisting of excipients, surface active agents, dispersing agents, sweetening agents, flavoring agents, coloring agents, preservatives, oily vehicles, solvents, suspending agents, dispersing agents, wetting agents, emulsifying agents, demulcents, buffers, salts, spreading agents, antioxidants, antibiotics, antifungal agents and stabilizing agents.

While drug excipients often improves physiochemical stability in solid dosage formulations, the presence of excipients in suspension formulations is another source of both chemical and physical variability that can impact influence final product. Moreover, many excipients are known to be toxic above certain individual thresholds or in combination with other excipients and/or APIs. Persons of ordinary skill in the art would understand that both the U.S. Food and Drug Administration (FDA), the World Health Organization (WHO) and other related entities list maximum recommended daily intake limits of drug excipients to avoid excipient mediated toxicities. The World Health Organization (WHO) has specified a maximum daily allowance limit for the following excipients present within the inventive formulation FIG. 15.

Non-limiting examples of excipients individually suspected of causing adverse events include: acacia, acesulfame, acesulfame potassium, acetic acid, acetone, acetyltributyl citrate, alcohol, alginic acid, alpha-tocopherol, aluminum chloride, aluminum chlorohydrex propylene glycol, aluminum hydroxide, aluminum lake dyes, aluminum oxide, aluminum silicate, aluminum stearate, aluminum sulfate, amide resin, aminobenzoate sodium, ammonia ammonio methacrylate copolymer, ammonio methacrylate copolymer type A, ammonio methacrylate copolymer type B, ammonio methacrylate copolymers, ammonium chloride, ammonium hydroxide, ammonium laureth-5 sulfate, ammonium phosphate dibasic, artificial flavor, artificial grape flavor, artificial mint flavor, ascorbic acid, ascorbyl palmitate, aspartame, aspartame powder, banana barium sulfate, benzalkonium chloride, benzoic acid, benzyl alcohol, betadex black currant, black currant flavor, black ink black pigment, blackberry, blue dye, butyl alcohol, butylated hydroxyanisole, butylated hydroxytoluene butylparaben, calcium, calcium carbonate, calcium phosphate, calcium phosphate dibasic anhydrous, calcium phosphate dihydrate dibasic, calcium silicate, calcium stearate, calcium sulfate, calcium sulfate anhydrous, calcium sulfate dehydrate, candelilla wax, candelilla wax powder, carbomer, carbomer 934, carbomer 934p, carbomer homopolymer type A, carbomer homopolymer type B, carbomer homopolymer type C, carboxymethylcellulose, carboxymethylcellulose calcium, carboxymethylcellulose sodium, carmine, carnauba wax, carrageenan, castor oil, castor wax, cellacefate, cellulose, cellulose acetate, cellulose compounds, cellulose powdered, cellulosic polymers, cetostearyl alcohol, cetyl alcohol, cetylpyridinium chloride, cherry, citric acid, citric acid anhydrous, citric acid monohydrate, cochineal, coconut oil colophony colorants, coloring agent, compressible sucrose, compressible sugar, confectioners sugar, copovidone, corn, corn oil, corn starch, corn syrup, corn syrup solids, corn-derived proteins, cottonseed oil, cranberry, croscarmellose sodium, croscarmellose sodium type A, crospovidone, cysteine hydrochloride, D&C Blue No. 1, D&C Green No. 5, D&C Red No. 21, D&C Red No. 22, D&C Red No. 27, D&C Red No. 27 Aluminum Lake, D&C Red No. 27 Lake, D&C Red No. 28, D&C Red No. 28 Aluminum Lake, D&C Red No. 30, D&C Red No. 30 Aluminum Lake, D&C Red No. 33, D&C Red No. 40, D&C Red No. 6, D&C Red No. 6 Lake, D&C Red No. 7, D&C Red No. 7 Calcium Lake, D&C Yellow No. 10, D&C Yellow No. 10 Aluminium Lake, D&C Yellow No. 10 Lake, D&C Yellow No. 5, D&C Yellow No. 6, dehydrated alcohol, dextrates, dextrose, dextrose monohydrate, dibasic calcium phosphate, dibutyl phthalate, dibutyl sebacate, dicalcium phosphate, diethyl phthalate, dihydroxyaluminum sodium carbonate, dimethicone, dimethylaminoethyl methacrylate-butyl methacrylate-methyl methacrylate copolymer, dimethylpolysiloxane docusate sodium, dyes, edetate calcium disodium, edetate disodium edible black ink, egg lecithin, erythrosine, erythrosine sodium, ethanolamine, ethyl acrylate-methyl methacrylate copolymer, ethyl alcohol, ethyl butyrate, ethyl isovalerate, ethylcellulose ethylcellulose (10 mPa·s), ethylcellulose (100 mPa·s), ethylcellulose (20 mPa·s), ethylcellulose (7 mPa·s), ethylcelluloses, ethylene glycol monoethyl ether, ethylvanillin, eudragit FD&C Blue No. 1, FD&C Blue No. 1 Aluminium Lake, FD&C Blue No. 1 Lake, FD&C Blue No. 2, FD&C Blue No. 2 Aluminium Lake, FD&C Blue No. 2 Lake, FD&C Green No. 3, FD&C Green No. 3 Aluminum Lake, FD&C Red No. 3, FD&C Red No. 4, FD&C Red No. 40, FD&C Red No. 40 Aluminium Lake, FD&C Red No. 40 Lake, FD&C Yellow No. 10, FD&C Yellow No. 10 Aluminum Lake, FD&C Yellow No. 10 Lake, FD&C Yellow No. 5, FD&C Yellow No. 5 Aluminum Lake, FD&C Yellow No. 5 Lake, FD&C Yellow No. 6, FD&C Yellow No. 6 Aluminum Lake, FD&C Yellow No. 6 Lake, ferric oxide, ferric oxide black, ferric oxide brown, ferric oxide orange, ferric oxide red, ferric oxide yellow, ferric oxides, ferrosoferric oxide, ferrous fumarate, ferrous oxide, flavor, flavors, fragrances, fumaric acid, gelatin, glucosamine, glucosamine hydrochloride, glutamic acid hydrochloride, glycerin, glycerol, glycerol monooleate, glycerol monostearate, glyceryl behenate, glyceryl distearate, glyceryl monooleate, glyceryl monostearate, glyceryl triacetate, glycine, glycolate, glycyrrhizin ammoniated, guar gum, hard gelatin capsule, hard paraffin, hydrochloric acid, hydrochloric acid, hydrogen peroxide, hydrogenated castor oil, hydrogenated cottonseed oil, hydrogenated soy oil, hydrogenated soybean oil, hydrogenated vegetable oil, hydroxyethyl cellulose, hydroxypropyl cellulose, hydroxypropyl methylcellulose, hydroxypropyl methylcellulose phthalate, hypromellose, hypromellose 2208, hypromellose 2208 (100 mPa·s), hypromellose 2208 (100000 mPa·s), hypromellose 2208 (15000 mPa·s), hypromellose 2208 (3 mPa·s), hypromellose 2208 (4000 mPa·s), hypromellose 2910, hypromellose 2910 (15 mPa·s), hypromellose 2910 (15000 mPa·s), hypromellose 2910 (3 mPa·s), hypromellose 2910 (5 mPa·s), hypromellose 2910 (50 mPa·s), hypromellose 2910 (6 mPa·s), hypromellose 2910 3 cp, hypromellose 2910 50 cp, hypromellose 2910 5 cp, hypromellose 2910 6 cp, hypromellose 3 cp, hypromellose 5 cp, hypromellose 6 cp, hypromellose phthalate, hypromelloses, indigotindisulfonate sodium, iron, isobutylparaben, isopropyl, isopropyl alcohol, lactitol, lactitol monohydrate, lactose, lactose anhydrous, lactose hydrous, lactose monohydrate, lecithin, lemon oil, leucine, light mineral oil, low substituted hydroxypropyl cellulose, magnesium, magnesium aluminum silicate, magnesium carbonate, magnesium hydroxide, magnesium oxide, magnesium oxide heavy, magnesium silicate, magnesium stearate, magnesium trisilicate, maleic acid, malic acid, maltodextrin, mannitol, medium-chain triglycerides, meglumine, menthol, methacrylic acid, methacrylic acid-ethyl acrylate copolymer (1:1) type a, methacrylic acid-methyl methacrylate copolymer (1:1), methacrylic acid-methyl methacrylate copolymer (1:2), methacrylic acid copolymer, methacrylic acid copolymer type B, methanol, methyl alcohol, methyl cinnamate, methyl methacrylate, methylcellulose, methylcellulose (100 mPa·s), methylcellulose (15 mPa·s), methylcellulose (400 mPa·s), methylene chloride, methylparaben, methylparaben sodium, microcrystalline cellulose, microcrystalline wax, mineral oil, mint, mint cream flavor, mint menthol, modified corn starch, monosodium citrate, natural and artificial orange flavor, natural flavor, natural mint flavor, natural peppermint flavor, natural resin, nonoxynol-100, oleic acid, olive oil, opacode black, orange cream flavor, orange juice, orange oil, orange-pineapple flavor, other ingredients known to those skilled in the art, palm kernel oil, paraffin, partially hydrogenated soybean and palm oils, peanut oil, peppermint, peppermint flavor, peppermint oil, pharmaceutical glaze, phenylalanine, phosphoric acid, piperazine, polacrilin potassium, polacrilin sodium, poloxamer, poloxamer 188, poloxamer 407, polyacrylate dispersion 30%, polycarbophil, polydextrose, polyethylene glycol, polyethylene glycol 1450, polyethylene glycol 300, polyethylene glycol 3000, polyethylene glycol 3350, polyethylene glycol 400, polyethylene glycol 4000, polyethylene glycol 600 polyethylene glycol 6000, polyethylene glycol 800, polyethylene glycol 8000, polygalacturonic acid, polyplasdone xl, polysorbate, polysorbate 20, polysorbate 80, polyvinyl acetate, polyvinyl alcohol, polyvinylpyrrolidone, potassium, potassium bicarbonate, potassium bitartrate, potassium carbonate, potassium carbonate anhydrous, potassium chloride, potassium gluconate, potassium hydroxide, potassium sorbate, potato starch, povidone, povidone k12, povidone k25, povidone k29/32, povidone k30, povidone k90, precipitated calcium carbonate, pregelatinized corn starch, pregelatinized starch, propyl gallate, propylene glycol, propylene glycol alginate, propylparaben, propylparaben sodium, raspberry, raw sugar, riboflavin, rice starch, saccharin, saccharin sodium, sd-45 alcohol, sda-3a alcohol, sesame oil, shellac, silicified microcrystalline cellulose, silicon dioxide, silicon dioxide colloidal, silicone, simethicone, simethicone emulsion, sodium, sodium alginate, sodium ascorbate, sodium benzoate, sodium bicarbonate, sodium carbonate, sodium carbonate monohydrate, sodium caseinate, sodium chloride, sodium citrate, sodium citrate dehydrate, sodium glycolate, sodium hydroxide, sodium laureth sulfate, sodium lauryl sulfate, sodium lauryl sulphate, sodium metabisulfite, sodium monolaurate, sodium phosphate, sodium phosphate dibasic, sodium propionate, sodium starch glycolate, sodium starch glycolate type A potato, sodium stearate, sodium stearyl fumarate, sodium thioglycolate, sodium tripolyphosphate, sorbic acid, sorbitan, sorbitan monolaurate, sorbitan monooleate, sorbitol, sorbitol special, soya lecithin, soybean oil, spearmint, starch, stearic acid, stearyl alcohol, strawberry, strawberry guarana flavor, strong ammonia solution, succinic acid, sucralose, sucrose, sucrose stearate, sugar 6× powder, sugar spheres, sunflower oil, synthetic ferric oxide, synthetic ferric oxide black, synthetic ferric oxide red, synthetic ferric oxide yellow, synthetic ferric oxides, tapioca starch, tartaric acid, tartrazine, taurine, TIMERx-N, titanium dioxide, titanium oxide, tragacanth, triacetin, tribehenin, tricalcium phosphate, triethyl citrate, trimyristin, trisodium citrate anhydrous, trisodium citrate dehydrate, tromethamine, tropical blend flavor, vanilla, vanilla flavor, vanillin, vitamin e, water, wax, wheat starch, white wax, xanthan gum, xylitol, yellow wax, zinc gluconate, zinc stearate.

Buffering systems affect the physical stability and appearance of drug formulations. A variety of buffering systems are known in the art and include various forms of acetates (especially acetic acid and sodium acetate), citrates (especially citric acid and sodium citrate), and phosphates (especially sodium phosphate and disodium phosphate). During the development process, addition of simethicone to the formulation resulted in an unacceptable marbled and thin suspension at higher API loading (100 mg/5 ml). Subsequent addition of a proprietary citrate:phosphate buffer system was shown to improve the appearance and physical stability of the inventive formulations across all product API strengths.

Alcohol, benzoates, parabens, phenols, quaternary ammonium compounds (i.e., quats), sorbic acid, salts and other substances generally known to one of skill in the art have all been employed as preservative agents for suspension formulations. A proprietary blend of methyl hydroxybenzoate and propyl hydroxybenzoate was selected as a preservative system as it demonstrated synergistic antimicrobial activity in the pH range of the inventive composition of matter.

All formulations showing product stability (e.g., 12.5 mg/5 ml, 25 mg/5 ml and 100 mg/5 ml) were scaled up as part of the process validation (PV) exercise. PV batches were manufactured using the final production equipment and facility to cGMP and compared to a reference product (SEROQUEL™ 25 mg Tablets) using dissolution (paddles 50 RPM) at three pH levels (i.e., 1.2, 4.5 and 6.8). Dissolution at all pH levels was equal to or greater than approximately 75% in 15 minutes, thus demonstrating bioequivalence. The outcome of bioequivalence studies revealed that the 25 mg/5 ml suspension was bioequivalent to SEROQUEL™ 25 mg tablets and the 100 mg/5 ml suspension was bioequivalent to SEROQUEL™ 100 mg tablet.

FIG. 16a describes the particle size and viscosity data for 12.5 mg/5 ml, 25 mg/5 ml and 100 mg/5 ml 10 L validation batches at 5° C. FIG. 16b describes particle sizes for additional production scale batches. FIG. 16c describes viscosity data for additional production scale batches.

FIG. 17 describes the 90% confidence intervals for quetiapine mean test/reference ratios. The 90% confidence intervals of the test/reference ratio for AUC and $C_{max}$ values for quetiapine lie within the acceptable limits of 80.00% to 125.00%, in line with the "Guideline on the Investigation of Bioequivalence (CPMP/EWP/QWP/1401/98 Rev 1/Corr**). Thus, the data support the claim that the disclosed 20 mg/ml oral liquid quetiapine suspension product is bioequivalent to the reference product SEROQUEL™ 100 mg film-coated tablets (Astra Zeneca UK Limited).

It is envisaged that the product would be supplied in an Amber glass (Type III) container with a childproof closure.

The present formulation is a novel and nonobvious improvement over previously described oral quetiapine formulations (both extemporaneously prepared aqueous and commercially approved solid formulations) because the inventive drug formulation allows for uniform and consistent delivery of drug substance to a patient in need thereof throughout the entire extended shelf life of the product.

Organoleptic ingredients improve the taste and appearance and do not negatively affect the suspension stability. The organoleptic agents in the following examples include coloring and flavoring agents, sweeteners and masking agents.

The suspension has antimicrobial activity as disclosed in FIG. 1. It is conceivable that other compatible antimicrobial excipients may also be used.

Mutual compatibility of the components means that the components do not separate in preparation and storage for up to the equivalent of two years at room temperature. Storage stability means that the materials do not lose their desirable properties during storage for the same period.

"Active agent" generally means a compound, macromolecule, element, substance, or mixture that when administered to a patient, alone or in combination with another compound, macromolecule, element, substance, or mixture, confers, directly or indirectly, a physiological effect on the patient. When the active agent is a compound, then salts, solvates (including hydrates), esters, and prodrugs of the compound are contemplated herein. Furthermore, crystalline forms, non-crystalline forms, polymorphs and any pseudopolymorphs of the compound are also contemplated herein.

"Bioavailability" generally means the extent or rate at which an active agent is absorbed into a living system or is made available at the site of physiological activity. Bioavailability can be characterized by one or more pharmacokinetic parameters. "Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. $AUC_{0-INF}$ is the calculated area under the curve of plasma concentration versus time from time 0 to time infinity. FIG. 18 describes the pharmacokinetic parameters of the inventive oral quetiapine fumarate liquid suspension product.

In some embodiments, the oral liquid suspension composition is bioequivalent to a reference drug. "Reference drug" means an active pharmaceutical ingredient product as described in the U.S. Federal Food and Drug Administration's (FDA) Orange Book, Approved Drug Products with Therapeutic Equivalence Evaluations or the European Medicines Agency (EMEA) document "Note for Guidance on the Investigation of Bioavailability and Bioequivalence. In a preferred embodiment, the reference drug is SEROQUEL™ approved by the U.S. FDA under NDA020639.

In one embodiment, the reference drug is a Seroquel®, i.e., a quetiapine fumarate product was initially described in U.S. Federal Food and Drug Administration's New Drug Application No. 20639 and approved for use on Sep. 26, 1997 and which is listed in the U.S. Federal Food and Drug Administration's Orange Book, as the RLD or "reference listed drug" for generic equivalents thereof.

Under U.S. FDA guidelines, two products (e.g. an inventive composition and brand drug) or methods (e.g., dosing under non-fasted versus fasted conditions) are bioequivalent if the 90% Confidence Interval (CI) limits for a ratio of the geometric mean of logarithmic transformed $AUC_{0\text{-}INF}$, $AUC_{0\text{-}t}$ and $C_{max}$ for the two products or two methods are about 0.80 to about 1.25.

To show bioequivalence between two compounds or administration conditions pursuant to Europe's EMEA guidelines, the 90% CI limits for a ratio of the geometric mean of logarithmic transformed $AUC_{0\text{-}INF}$, $AUC_{0\text{-}t}$ for the two products or methods are about 0.80 to about 1.25. The 90% CI limits for a ratio of the geometric mean of logarithmic transformed $C_{max}$ for the two products or methods can have a wider acceptance range when justified by safety and efficacy considerations.

"Bioequivalence" means the absence of a significant difference in the rate and extent to which the active agent or surrogate marker for the active agent in pharmaceutical equivalents or pharmaceutical alternatives becomes available at the site of action when administered in an appropriately designed study.

The term "pharmaceutically acceptable" generally means suitable for use in contact with the tissues of humans and animals without undue toxicity, irritation, allergic response, and the like, commensurate with a reasonable benefit/risk ratio, and effective for their intended use within the scope of sound medical judgment.

By "pharmaceutically effective amount", it is generally meant the amount of an active agent that, when administered to a patient for treating a disease, is sufficient to effect such treatment for the disease. A pharmaceutically effective amount will vary depending on the active agent, the disease and its severity, and the age, weight, and other conditions of the patient to be treated.

"Salts" include derivatives of an active agent, wherein the active agent is modified by making acid or base additions thereof.

"Solvate" means a complex formed by solvation (the combination of solvent molecules with molecules or ions of the active agent of the present invention), or an aggregate that consists of a solute ion or molecule (the active agent of the present invention) with one or more solvent molecules.

"Shelf Stability" generally refers to the longest length of time in the labeling or approval documentation accompanying a commercially approved drug formulation. In an embodiment, the labeling or approval documentation originates from the European Medicines Agency. In another embodiment, the labeling or approval documentation originates from the U.S. Food and Drug Agency (FDA).

"D(0.9) value" refers to the threshold at which 90% of the particles in a sample are expected to be smaller as measured by particle size diameter. Unless noted otherwise, all D(0.9) values are in μm.

The foregoing describes the invention, including preferred forms thereof, alterations or modifications as would be understood to a person skilled in this particular art are intended to be included within the scope of the invention as claimed. In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The described embodiments of the invention may be modified or varied, and elements added or omitted, without departing from the invention, as appreciated by those skilled in the art in light of the disclosed teachings. Each reference cited herein is incorporated by reference as if each were individually incorporated by reference.

We claim:

1. A pharmaceutical composition comprising a pharmaceutically effective amount of quetiapine fumarate particles dispersed in suspension, wherein the composition is suitable for oral delivery, has a pH between about 5.0 and 6.0, and is storage stable.

2. The composition of claim 1, wherein the composition viscosity is approximately 700-2000 cP.

3. The composition of claim 2, wherein the quetiapine fumarate concentration is 12.5 mg/5 ml.

4. The composition of claim 2, wherein the quetiapine fumarate concentration is 25 mg/5 ml.

5. The composition of claim 2, wherein the quetiapine fumarate concentration is 100 mg/5 ml.

6. The composition of claim 2, wherein the quetiapine fumarate concentration is 200 mg/5 ml.

7. The composition of claim 5 that is bioequivalent to commercially approved solid dosage formulations of quetiapine fumarate.

8. The composition of claim 1 that is at least 24-month storage stable at 2 to 8 degrees centigrade.

9. The composition of claim 1, wherein approximately ninety percent of the quetiapine fumarate starting material has a maximum particle diameter between 20 μm and 70 μm.

10. The composition of claim 1, wherein the D(0.9) value of the 12.5 mg/5 ml final product is approximately 60 to 120 μm and viscosity approximately 1050 to 1800 cP.

11. The composition of claim 1, wherein the D(0.9) value of the 25 mg/5 ml final product is approximately 60 to 120 μm and viscosity approximately 790 to 1200 cP.

12. The composition of claim 1, wherein the D(0.9) value of the 100 mg/5 ml final product is approximately 60 to 120 μm and viscosity approximately 1180 to 1400 cP.

13. The composition of claim 1, wherein about 70% or more of the quetiapine fumarate is fully dissolved in 45 minutes.

14. The composition of claim 1, wherein the quetiapine fumarate is substantially comprised of the Form 1 polymorph.

15. A process for the manufacture of a pharmaceutical composition comprising a pharmaceutically effective amount of quetiapine fumarate particles dispersed in suspension comprising:
    adding purified water to a main vessel,
    adding citric acid monohydrate to the main vessel and mixing until dissolved using a high-shear mixer,
    adding disodium hydrogen phosphate dihydrate to the main vessel and mixing until dissolved using a high-shear mixer,
    adding sucralose to the main vessel and mixing until dissolved using a high-shear mixer,
    adding the simethicone emulsion to the main vessel and mixing until dispersed using a high-shear mixer, adding quetiapine fumarate to the main vessel and mixing using a high-shear mixer until a homogeneous suspension is produced, to a separate stage vessel adding propylene glycol, to the separate stage vessel adding methyl hydroxybenzoate, to the separate stage vessel adding propyl hydroxybenzoate and mixing using a high-shear mixer until dissolved, to the preservative solution in the separate stage vessel adding xanthan gum and mixing until homogenous using a propeller mixer, adding the preservative solution/xanthan gum slurry in the separate stage vessel to the main vessel and mixing using a high-shear mixer until a uniformly thickened suspension is produced, adding the lemon flavour to the main vessel and mixing with a high-shear mixer until dispersed, checking the pH of the solution (target pH is 5.50), wherein if the pH is outside the range of 5.2-5.8 adjusting the pH until it within this range by using either 10% w/v citric acid monohydrate solution to lower pH or a 10% w/v disodium hydrogen phosphate dihydrate solution to increase the pH, adding purified water to final volume and mixing until dispersed using a high-shear mixer, filling 152±2 ml of finished product into 180 ml amber glass bottles and closing with child resistant closures.

* * * * *